(12) United States Patent
Poulos

(10) Patent No.: US 8,480,748 B2
(45) Date of Patent: *Jul. 9, 2013

(54) LORDOTIC EXPANDABLE INTERBODY IMPLANT AND METHOD

(76) Inventor: Nicholas Poulos, Belleville, IL (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/030,618

(22) Filed: Feb. 18, 2011

(65) Prior Publication Data

US 2012/0089228 A1 Apr. 12, 2012

Related U.S. Application Data

(63) Continuation-in-part of application No. 12/899,625, filed on Oct. 7, 2010.

(51) Int. Cl.
*A61F 2/44* (2006.01)

(52) U.S. Cl.
USPC ........................................ 623/17.16; 606/279

(58) Field of Classification Search
USPC ........................................... 623/17.11–17.16
See application file for complete search history.

(56) References Cited

U.S. PATENT DOCUMENTS

| | | | |
|---|---|---|---|
| 6,080,193 A | 6/2000 | Hochshuler et al. | |
| 6,997,929 B2 | 2/2006 | Manzi et al. | |
| 7,311,713 B2 | 12/2007 | Johnson et al. | |
| 7,445,637 B2 * | 11/2008 | Taylor | 623/17.16 |
| 7,967,862 B2 * | 6/2011 | Allard et al. | 623/17.11 |
| 2003/0139815 A1 * | 7/2003 | Grooms et al. | 623/17.11 |
| 2003/0187506 A1 | 10/2003 | Ross et al. | |
| 2005/0055029 A1 | 3/2005 | Marik et al. | |
| 2005/0187559 A1 | 8/2005 | Raymond et al. | |
| 2006/0116768 A1 | 6/2006 | Krueger et al. | |
| 2006/0129243 A1 * | 6/2006 | Wong et al. | 623/17.16 |
| 2007/0093898 A1 * | 4/2007 | Schwab et al. | 623/17.11 |
| 2007/0162128 A1 * | 7/2007 | DeRidder et al. | 623/17.11 |
| 2007/0162131 A1 * | 7/2007 | Friedman et al. | 623/17.11 |
| 2008/0021555 A1 | 1/2008 | White et al. | |
| 2008/0125864 A1 * | 5/2008 | de Villiers et al. | 623/17.15 |
| 2008/0221687 A1 * | 9/2008 | Viker | 623/17.16 |
| 2008/0288073 A1 * | 11/2008 | Renganath et al. | 623/17.12 |
| 2009/0054990 A1 * | 2/2009 | Myint et al. | 623/17.16 |

OTHER PUBLICATIONS

PCT International Search Report dated Jun. 20, 2011, for the International Application No. PCT/US2010/051984, International Filing Date Oct. 8, 2010.

(Continued)

*Primary Examiner* — Ellen C Hammond
*Assistant Examiner* — Atiya Mahmud
(74) *Attorney, Agent, or Firm* — Polster Lieder Woodruff & Lucchesi, L.C.

(57) ABSTRACT

The present disclosure relates to an intervertebral implant that can be surgically introduced between adjacent vertebral bodies and adjusted or expanded in situ to occupy an optimal or desired space between the vertebral bodies. The implant is preferably inserted into the evacuated disc space obliquely and then oriented so as to extend laterally across the anterior adjacent vertebrae bodies occupying the disc space with the outer ends of the implant being supported by the cortical rims on the opposite sides of the vertebrae bodies. The implant has two body members with a space therebetween so the implant may be then distracted and a spacer of a, predetermined thickness may be inserted within the space between the body members so as to maintain a desired amount of distraction. The upper and lower surfaces of the implant may have a desired lordotic angle. A method of using an implant is also disclosed.

6 Claims, 33 Drawing Sheets

OTHER PUBLICATIONS

PCT Written Opinion of the International Searching Authority dated Jun. 20, 2011, for the International Application No. PCT/US2010/051984, International Filing Date Oct. 8, 2010.
SpineWave StaXx® XD Expandable Device—In Situ Distraction Minimal Retraction web page by Spine Wave, Inc. of Shelton, CT.
Medtronic Capstone Peek Spinal System PLIF and TLIF Brochure.
CoRoent XLIF brochure by NuVasive.
Lucent Lumbar InterBody—Setting Our Sights on Simplicity brochure.
AVS PEEK Spacer Portfolio General Systems Overviews—Stryker's PEEK Solution brochure published by Stryker Spine of Allendale, NJ. Copyright 2008.
Surgeon-focused Eduction—MAS—Maximum Access Surgery by NuVasive, Inc. of San Diego, CA. Copyright 2007.
XLIF Throacic Surgical Technique brochure by NuVasive, Inc. of San Diego, CA. Copyright 2007.
XLIF Surgical Techniques—MaXcess II brochure by NuVasive of San Diego, CA. Copyright 2006.
AVS UniLIF PEEK Spacer System brochure by Stryker Spine, Inc. of Allendale, NJ. Copyright 2010.
Verte-Stack Crescent PEEK Vertebral Body Spacer brochure by Medtronic Spinal and Biologics Business, Memphis, TN. Copyright 2008.
CD Horizon Legacy 5.5, a Masterpiece in Medical Device Design Brochure by Medtronic Sofamor Danek.
AVS TL PEEK Spacer Implant, Stryker Spine, Inc. of Allendale, NJ. Web. <www.striker.com/en-us/products/Spine/InterbodyVertebralBodyReplacement/AVSTLPEEKSpacerImplant/index.htm> Printed Mar. 4, 2011.

* cited by examiner

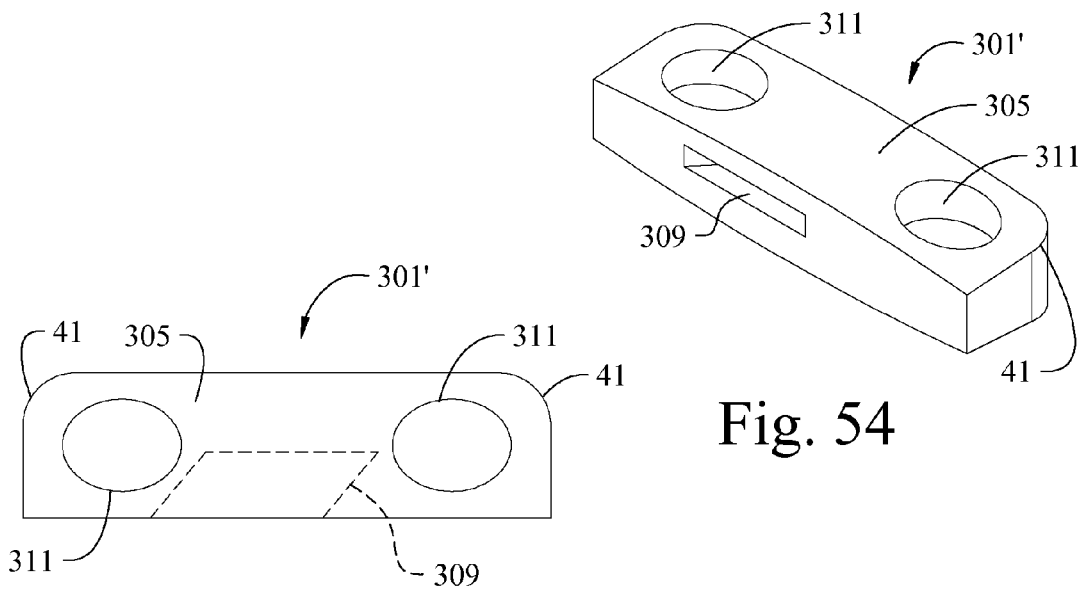
Fig. 54
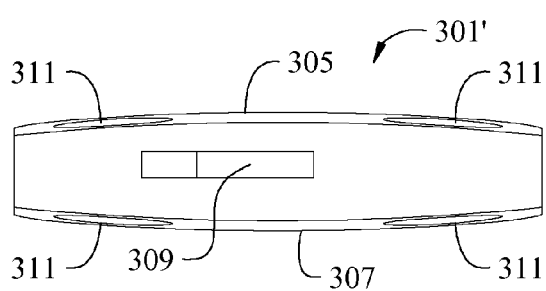
Fig. 55
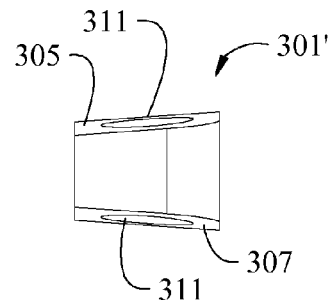
Fig. 58
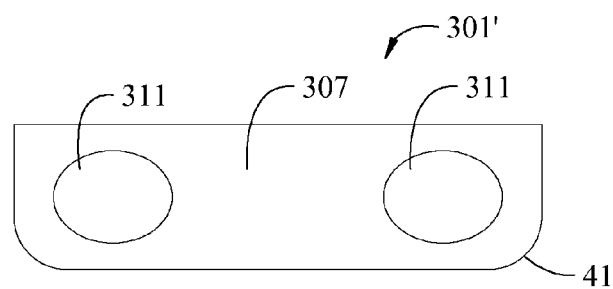
Fig. 56
Fig. 57

LORDOTIC EXPANDABLE INTERBODY IMPLANT AND METHOD

CROSS-REFERENCE TO RELATED APPLICATIONS

This application is a continuation-in-part and claims priority to U.S. patent application Ser. No. 12/899,625, filed Oct. 7, 2010. These prior applications are incorporated by reference in their entirety herein.

STATEMENT REGARDING FEDERALLY SPONSORED RESEARCH OR DEVELOPMENT

Not Applicable.

BACKGROUND OF THE DISCLOSURE

This disclosure relates to intervertebral disc prostheses, and more particularly to an intervertebral disc prosthesis that can be surgically introduced between adjacent vertebral bodies, preferably between lumbar vertebrae, and adjusted or expanded in situ to occupy an optimal or desired space between the vertebral bodies.

In recent years, surgical procedures have been developed in which two or more vertebrae are joined or fused together. Such procedures are now common in the treatment of spinal disorders such as spondylolisthesis, scoliosis, and disc degeneration. Certain of these fusion surgeries include Posterior Lumbar Interbody Fusion (PLIF), Transforaminal Lumbar Interbody Fusion (TLIF), Anterior Lumbar Interbody Fusion (ALIF), and DLIF (Direct Lateral Interbody Fusion). These procedures are well known to spinal surgeons.

Interbody vertebral spacers are known that are inserted between the vertebrae bodies to replace a collapsed, degenerated, or unstable disc. However, these prior spacers were typically of a predetermined thickness and thus it was difficult to size the thickness of the spacer to result in the desired amount of distraction between the vertebrae bodies in order to achieve the desired amount of distraction between the adjacent vertebra bodies. Such prior spacers are commercially available from Stryker Spine of Mahwah, N.J., from Medtronic, Spinal and Biologics Business, Memphis, Tenn., from Spinal Concepts, Inc. of Austin Tex., and from NuVasive, Inc. of San Diego, Calif.

Certain adjustable height interbody fusion devices are known, such as described in U.S. Pat. No. 6,080,193 that vary the distance between the portions of the spacer that engage the endplates of the adjacent vertebrae. However, these adjustable fusion devices rely on cam and other complicated mechanisms for adjustment purposes.

In general, lordosis is the curvature of the spine with the convexity forward. Lordosis is not necessarily a disease state, but rather the normal anterior physiologic curve of the neck or low back. This disclosure is primarily concerned with lumbar lordosis. Most lumbar disc spaces in healthy spines are generally parallel or nearly 0 degree lordotic, and is particularly true for L1/2, L2/3, and L 3/4 However, the L4/5 may have a lordotic angle ranging between about 0°-12°, and L5/S1 may also range between about 0°-12°. Therefore, in reconstructing a disc space that has some lordosis it would be advantageous to have an implant matching the existing anatomy so that the two surfaces of the implant would better conform to and better fit the shape of the disc space so that load sharing occurs over the whole implant. Otherwise, an implant having parallel upper and lower surfaces used in a disc space having, for example, 8 degrees of in situ lordosis would result in only part of the implant contacting its respective vertebrae bodies and therefore lessening the corrective support applied to the spine and thus predisposing the implant to subsidence. That is, subsidence refers to an increased tendency of the implant, over time, to telescope, settle or project into the adjacent vertebrae bodies with loss disc space height back to preoperative levels. When using conventional implants, it is frequently observed that such telescoping or settling occurs with such implants placed wholly within the disc space, rather than having the implant bearing on and distracting from the cortical rim/apophyseal ring of the adjacent vertebrae as disclosed in my co-pending U.S. patent application Ser. No. 12/899, 625. Additionally, a more conformal fit in a disc space with lordosis will allow more uniform distribution of corrective forces applied during distraction. Thus, it would be desirable to provide an expandable (variable height) implant, as described in my above-noted pending application that would provide options for encountered or desired disc space lordosis. It would also be desirable to use either a variable or a fixed height implant that could reconstruct any disc space anatomy or morphology surgically encountered including lordotic conditions with the surgical procedures described in my above-identified U.S. Patent applications and in the present disclosure.

SUMMARY OF THE DISCLOSURE

The present disclosure relates to an intervertebral disc prostheses, and more particularly to an intervertebral disc prosthesis that can be surgically introduced between adjacent vertebral bodies, preferably between lumbar vertebrae, and adjusted or expanded in situ to occupy an optimal or desired space between the vertebral bodies. The implant is preferably inserted into the evacuated disc space obliquely and then oriented so as to extend laterally across the adjacent vertebrae bodies anteriorly occupying the disc space with the outer ends of the implant being supported by the cortical rims on opposite sides of the adjacent vertebrae bodies. The outer convex surfaces of the two body members conform anatomically to the shape of the disc space contacting the endplates. The implant has two body members that are movable relative to one another so as to vary the space between the members. With the implant so positioned and oriented, the implant and thus the disc space may be then distracted and a spacer of a desired, predetermined thickness may be inserted within the space between the body members so as to maintain a desired amount of distraction.

Still further, the present disclosure relates to such an expandable (variable height) or non-expandable (fixed height) disc prosthesis that may have angled upper and lower surfaces engageable with the adjacent vertebrae bodies so as to introduce a predetermined degree of lordosis thereby to better reconstruct the spine by introducing segmental lordosis and improving regional lordosis and global sagittal balance. It is also understood that 0° or parallel surfaced implants maybe an appropriate choice dictated by intraoperative findings and surgical anatomy.

BRIEF DESCRIPTION OF THE DRAWINGS

FIG. 54 is a perspective view of still another non-expandable embodiment of the implant of this disclosure where such implant is fenestrated having openings therein and where such implant may be readily utilized in accordance with the methods of this disclosure;

FIG. 55 is a top plan view of the implant of FIG. 54;

FIG. 56 is a front elevational view of the implant of FIGS. 54, 55;

FIG. 57 is a bottom plan view of the implant of FIGS. 54-57;

FIG. 58 is a side elevational view of the implant of FIGS. 54-57 illustrated the angles upper and lower surfaces of the implant.

Corresponding reference characters indicate corresponding parts throughout the several views of the drawings.

DESCRIPTION OF PREFERRED EMBODIMENTS

Figure 1:
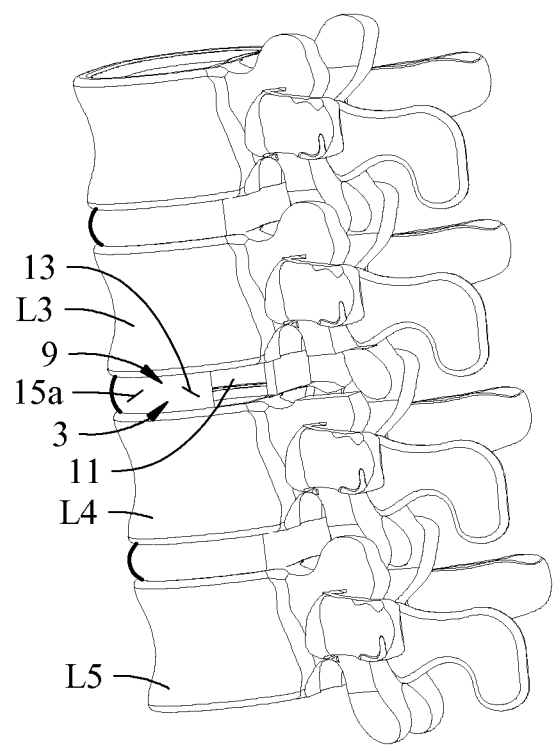
FIG. 1 is a ventral view of a series of lumbar vertebrae illustrating intervertebral cartilage discs between adjacent vertebrae; and further illustrating the locations of openings on opposite lateral sides of the annulus for the retention of a lumbar disc replacement implant or prosthesis of the present disclosure within the disc space between adjacent vertebrae.
Figure 2:
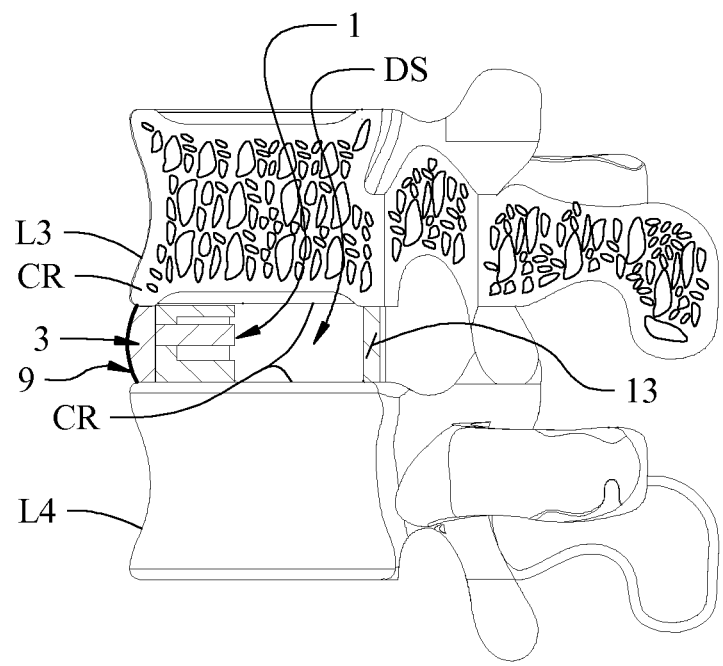
FIG. 2 is a median sagittal cross section of two adjacent lumbar vertebrae and certain of their ligaments illustrating the desired position of the lumbar disc replacement implant within the disc space.
Figure 3:
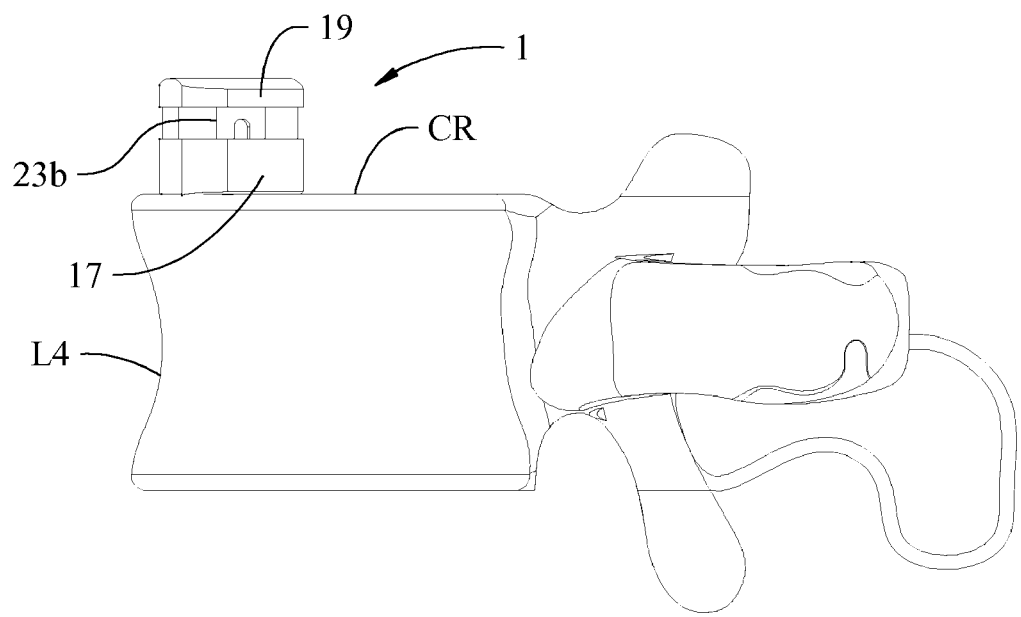
FIG. 3 is a side elevational view of a lumbar vertebrae illustrating the lateral placement of the implant on the upper surface of the cortical rim of the lower vertebrae body.

Referring now to the drawings and particularly to FIGS. 1-4C, a first embodiment of a lumbar disc implant device of the present disclosure is generally indicated at 1 (see FIG. 2), and is shown in its intended environment installed within the disc space DS between two adjacent human vertebrae to be fused together. Oftentimes the intervertebral disc 3 between two adjacent vertebrae (e.g., between lumbar vertebrae L3 and L4, or between lumbar vertebrae L4 and L5) may become degenerated and mechanically incompetent with subsequent loss of height between the adjacent vertebrae with resultant pain and loss of motion. It has become common practice to surgically reconstruct the degenerated disc 3 between the opposing surfaces of the vertebrae bodies and to insert a structural implant within the disc space between the vertebrae so as to space the vertebrae apart a desired distance thus restoring disc space height, and to bear normal biomechanical loads in the spine until a solid spinal fusion occurs. As is conventional, bone graft material (not shown) is introduced into the disc space for fusing the adjacent vertebrae together as the bone graft material grows. Also, such prior disc structural implants are stabilized by known vertebrae fixation devices, such as pedicle screw and rod fixation, which are widely known, but are not shown in the drawings.

Figure 4:
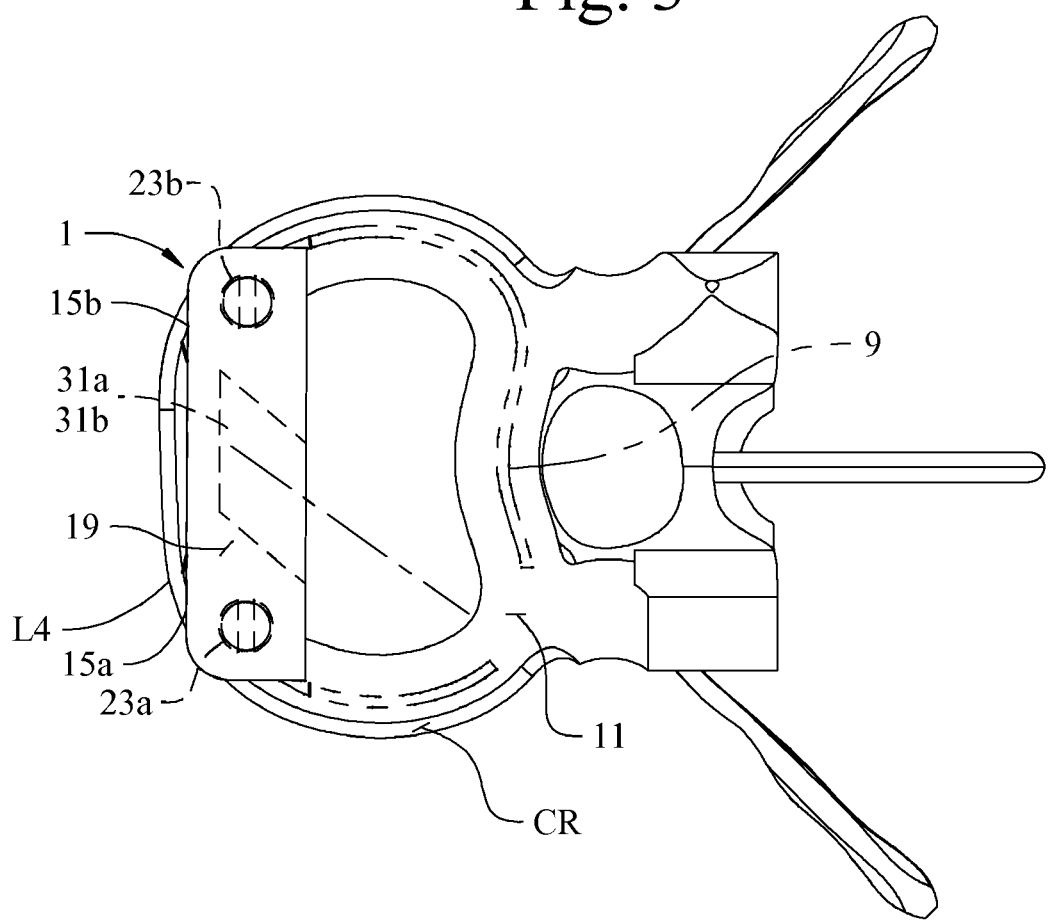
FIG. 4 is an axial view of a lumbar vertebrae illustrating the implant of the present disclosure which is initially inserted obliquely through an incision in the annulus (shown in phantom) with the implant oriented to extend laterally of the vertebrae bodies and to span from one side to the other of the vertebrae bodies and to bear against the cortical rims of the upper and lower vertebrae bodies and contacting the interposed endplate. This view further illustrates an oblique slot in the inner faces of the upper and lower implant body members so as to permit a surgical instrument (e.g., a parallel distractor) to be inserted in these slots to distract the disc space.
Figure 4A:
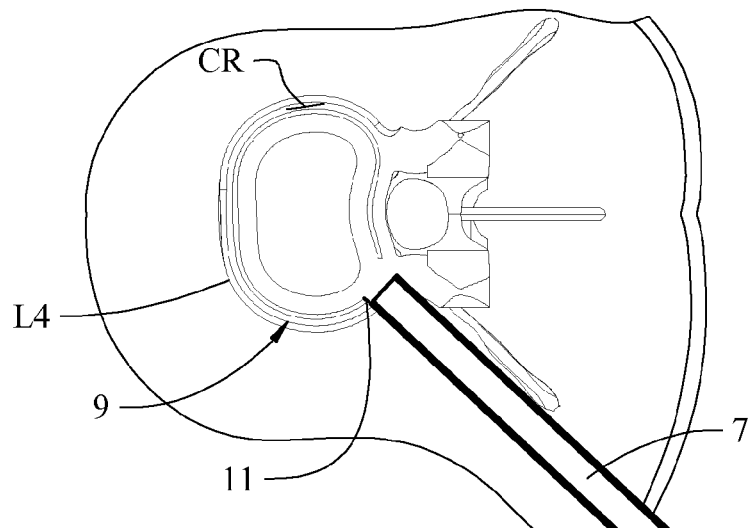
FIG. 4A is a transverse cross-sectional view of the spine illustrating a minimally invasive TLIF exposure dissecting between the fascial planes of the multifidus and longisimus muscles with an operative tube seated on the bony anatomy of the spine.

As shown in FIG. 4A, an approach is made generally in accord with known transforaminal interbody fusion (TLIF) procedures. Specifically, with the patient in a prone position, fluoroscopy localization is used to place an incision at the desired level. Either an open approach or an approach using a tubular retractor 7, as shown in FIG. 4A, may be used, as is well know in the art. Such a posterolateral TLIF approach is familiar to spine surgeons and does not risk the great vessels and abdominal viscera associated with ALIF (Anterior Lumbar Interbody Fusion) procedures nor does such an approach require an anterior access surgeon. Further, the TLIF approach does not risk injury to the lumbar plexus.

Figure 4B:
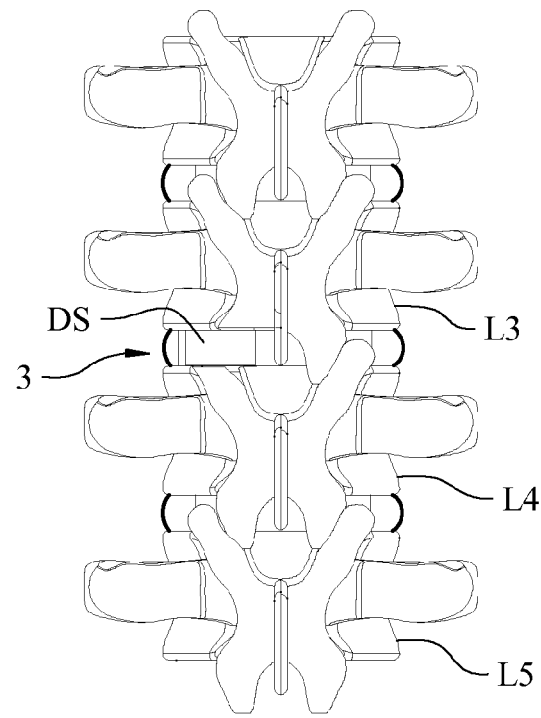
FIG. 4B illustrates lumbar vertebrae L3, L4 and L5 with a unilateral exposure of the operating site between vertebrae L5 and L4.

Further as shown in FIG. 4B, transforaminal access to the disc space DS between the vertebrae is achieved by resection of the inferior facet of L4, a portion of the pars interarticularis, and a portion of the superior facet of L5. Distraction (i.e., the forcing apart or separation of the vertebrae surfaces) to improve the working corridor may be achieved by using a laminar spreader or pedicle screws, both of which are well-known in the art and which are therefore not shown. Discectomy or removal of the disc material from within the annulus 9 is performed through an annulotomy 11, preferably, but not necessarily, a posterior oblique annulotomy, within the operative field (shown in FIGS. 1 and 4C) made in the wall 13 of the annulus 9. Endplate preparation follows using standard procedures and instruments including cupped curettes, ring curettes, box curettes, broaches, box chisels, rasps, and pituitary rongers. All of the disc material between the adjacent vertebrae bodies is removed while the walls 13 of annulus 9 are preserved. The cartilaginous endplates of the vertebrae are removed down to bleeding bone, but care is taken to preserve the cortical endplate, especially anteriorly.

Figure 4C:
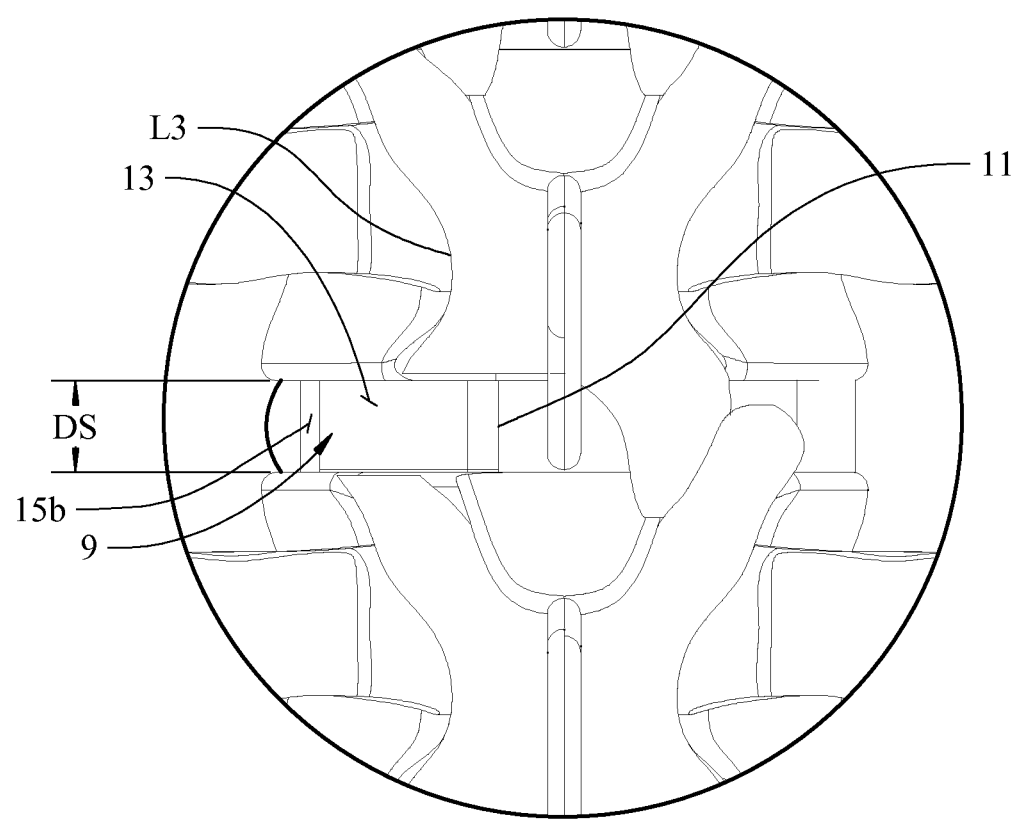
FIG. 4C is a lateral view of the operating site on a somewhat enlarged scale.

More specifically and as shown in FIG. 4C, incision (annulotomy) 11 in annulus 9 permits perforations or openings 15*a*, 15*b*, as best shown in FIG. 4, to be made in opposite lateral sides of the anterior annulus such that these openings are generally laterally symmetrical. Those skilled in the art will recognize that a surgeon having access to the interior of the disc space DS via incision 11 will, with proper vision magnification (e.g., a loupe), be able to make a first opening 15*a* distal from and somewhat to the anterior from incision 11. Then, the surgeon can make the second opening 15*b* generally across the annulus from the first opening 15*a* on the opposite anterolateral side of the disc. These annulotomies also serve as anterior releases to facilitate disc space DS distraction. More specifically, these anterior annulotomies 15*a*, 15*b* may be further relaxed using a variety of techniques including the use of so-called "trials" and distractor instruments, as are well known to those skilled in the art. It is common for surgeons to utilize metal trial implants (not shown) for gaging the size of the actual implant to be used where the trial is at least in part shaped like the implant 1 to be used. Such trials are typically provided in a range of widths, lengths and heights. With the disc space DS at least partially distracted, the surgeon will install a first trial, typically of a smaller size, length, width or height than the implant 1 that will be finally installed, through the anterior annulotomies. These trials are used to aid in distracting the vertebrae and to hold the vertebrae in this desired distracted position. After the ligaments and the annulus at least partially relax, further distraction of the disc space may be accomplished by actuation of a parallel distractor applied to the anterior annulotomies bilaterally. Another trial, typically somewhat larger than the first trial, may be inserted if further relaxation of the anterior annulotomies is required. It will be understood that the trials can be used to judge the width and height of the size of the actual implant 1 to be employed. Then, with the disc space DS prepared, the implant 1 of the proper height, length, and width will be installed, preferably in the manner discussed below.

Implants 1 are available in a series of various predetermined lengths, widths and heights to best fit particular patients. For example, the length of a typical implant 1 may be about 40 mm and about 8.5 mm tall. Calipers or trials (not shown) are used to measure and size the anterior disc space and to determine the length of the implant 1 to be used. Intraoperative fluoroscopy will aid in these measurements.

With the desired final height, width and length of the implant 1 determined, and with the implant in its collapsed or retracted position (for example, with spacer 35 removed from between the body members 17 and 19), the implant is inserted into the disc space DS via incision 11 at an oblique angle using the implant applicator (not shown) or other suitable instrument. The implant applicator grasps the implant firmly allowing controlled insertion and positioning of the distal end of the implant thru the contralateral anterior annulotomy 15*a*. Once the proximal end of the implant is within the disc space DS, the applicator is removed. The proximal end of the implant is tamped down so the implant is positioned in the anterior disc space. The parallel distractor may be used to maneuver implant into final position with both ends protruding through anterior annulotomies 15*a*, 15*b*, generally as shown in FIG. 4.

In this manner, the implant bears against and is supported by the cortical rim CR of both the upper and lower vertebrae. Fluoroscopic confirmation (as hereinafter described) of optimal positioning utilizing radiographic markers, as indicated at 43 in FIGS. 5 and 6, embedded in the implant is carried out. After the implant 1 has been so oriented and positioned within the disc space DS, the blades of a parallel distractor (not shown) are inserted into the disc space via incision 11 in the annulus 9. The disc space and the implant are then further distracted and a spacer, as indicated at 35 and as shown below, is installed within the implant in a manner as will appear. Upon removal of the parallel distractor and upon applying compression to the construct, the implant bodies 17, 19 and the spacer 35 will maintain the implant 1 in its desired height.

Figure 5:
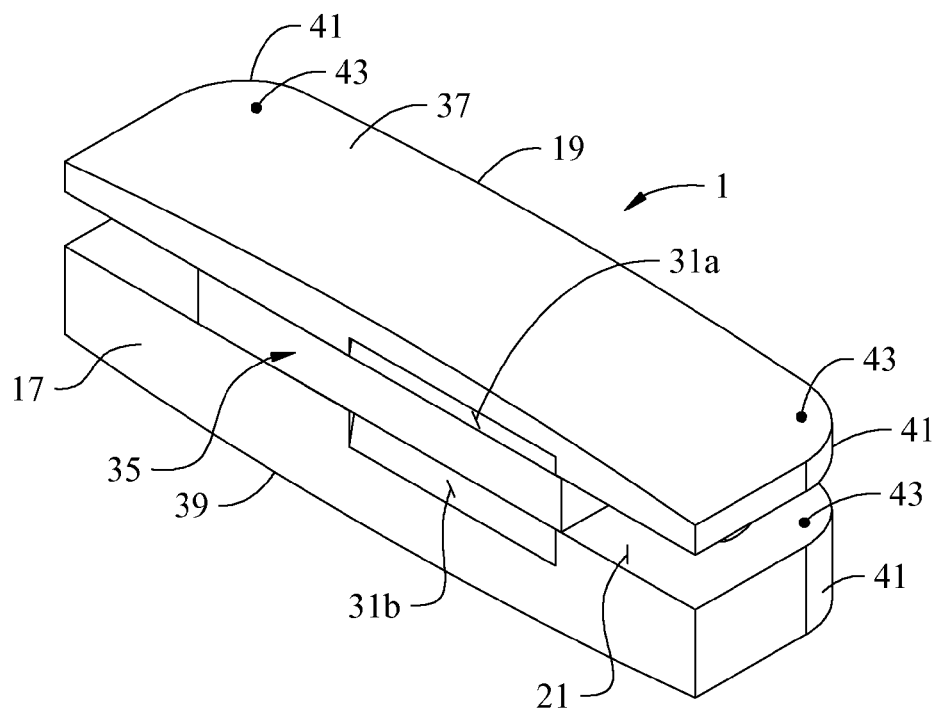
FIG. 5 is a posterior perspective view on an enlarged scale of the implant of the present disclosure, as viewed from above, having an upper and a lower body member with a space between the inner faces of these upper and lower body members and with a spacer of predetermined thickness inserted within the space between the body members so that when the disc space is retracted, the body members and the spacer maintain a desired distraction between the adjacent vertebrae bodies and bear normal spinal biomechanical loads until solid spinal fusion is achieved.

Referring now to FIGS. 5-17, the implant 1 of the present disclosure will now be described in detail. As shown in FIG. 5, implant 1 has a pair of separate body members 17 and 19, with body member 17 being referred to as a lower body member and with body member 19 being referred to as an upper body member with a space 21 therebetween. It will be appreciated that with the inner faces of the body members touching one another the space 21 is minimized and the overall height of the implant is minimized. With implant 1 in this position, it has a low profile that facilitates insertion and final positioning within disc space DS. Further, with the body members 17 and 19 spaced apart a maximum distance, the implant is in its fully distracted position. The height of implant 1 thus may be in situ expanded a desired amount to enable distraction of the degenerated disc 3 to normal anatomic height with appropriate tensioning of the annulus 9 and stabilizing ligaments.

Figure 13:
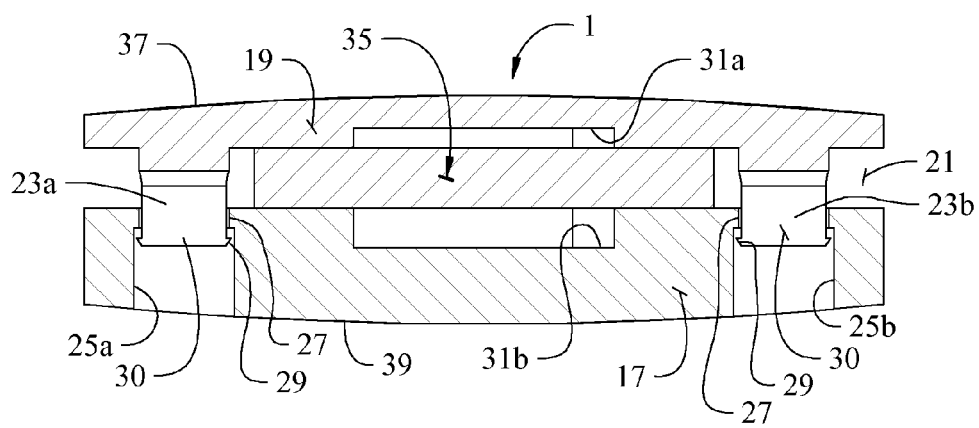
FIG. 13 is a lengthwise vertical cross sectional view taken along line 13-13 of FIG. 12.
Figure 14:
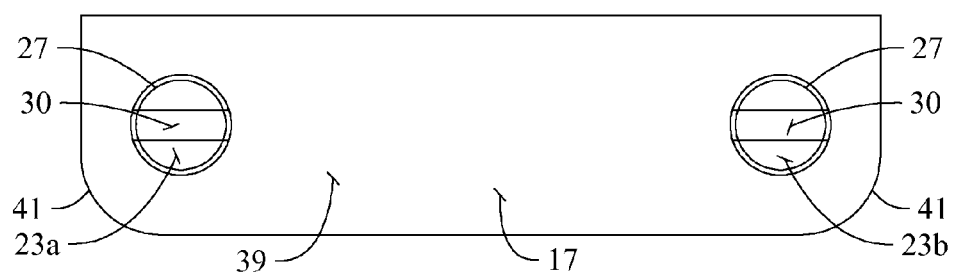
FIG. 14 is a bottom plan view of the implant.
Figure 15:
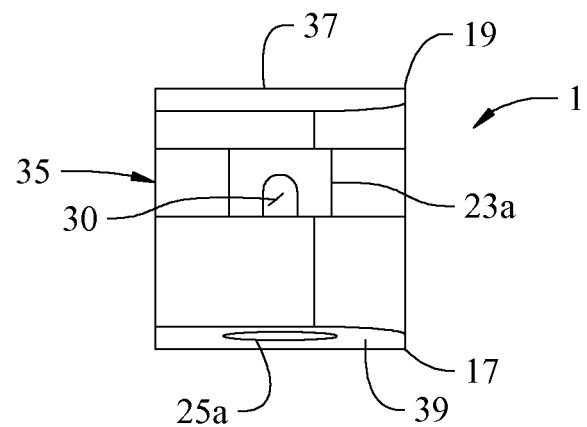
FIG. 15 is a right side elevational view of the implant as shown in FIG. 12.
Figure 16:
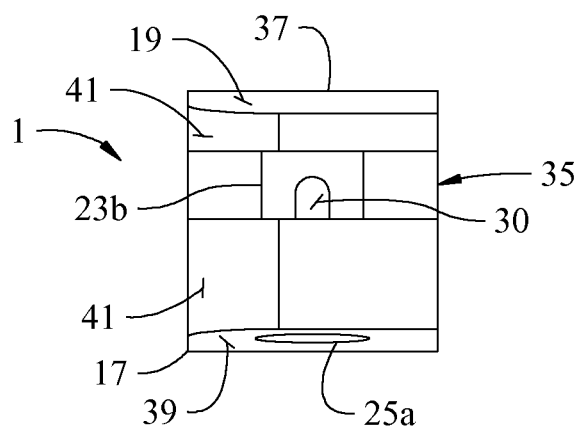
FIG. 16 is a left side elevational view of the implant as shown in FIG. 12.
Figure 17:
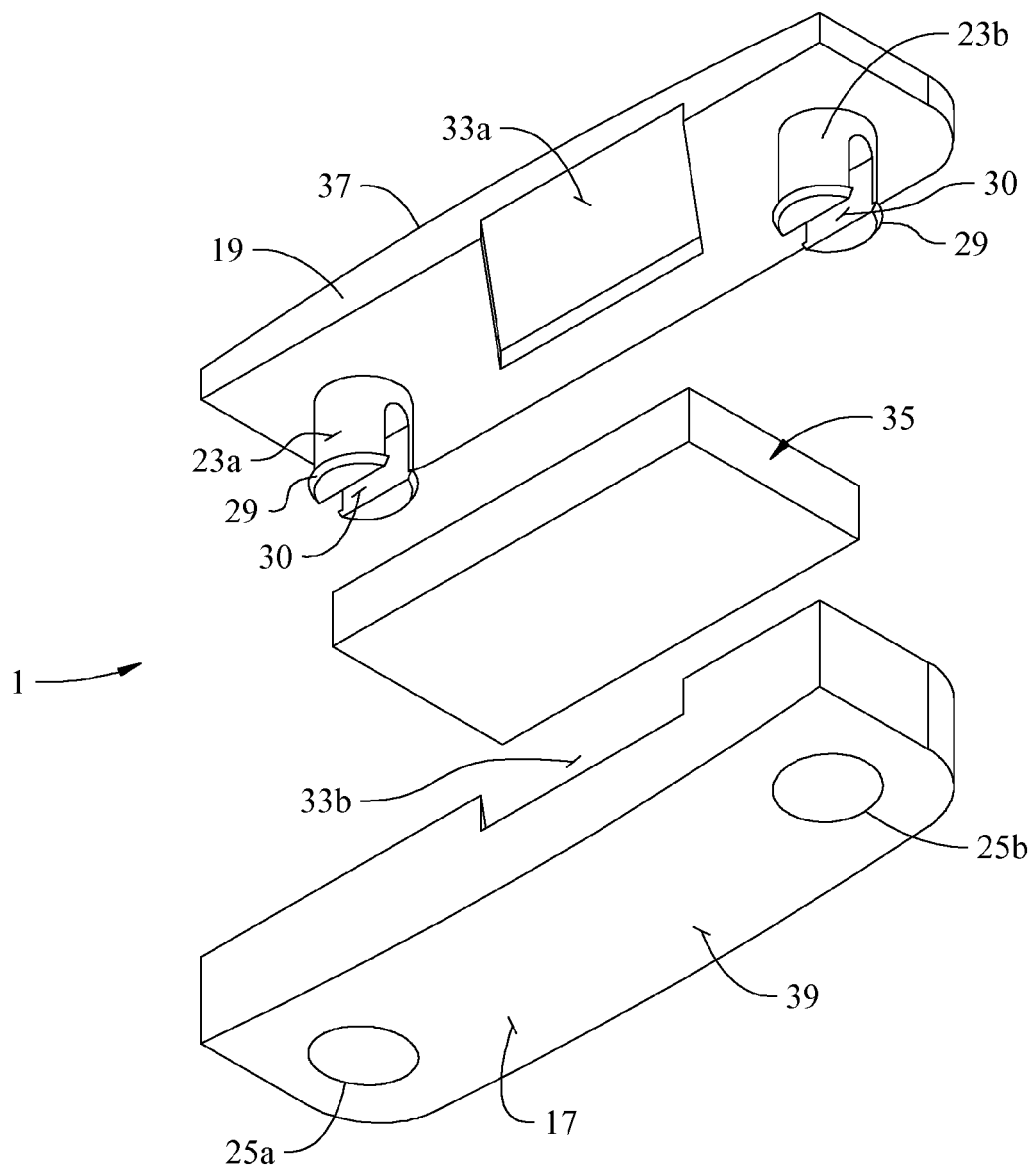
FIG. 17 is a bottom perspective exploded view of the implant.

As best shown in FIG. 13, the upper member 19 has a pair of spaced stabilizing posts 23*a*, 23*b* extending down into space 21. These stabilizing posts 23*a*, 23*b* are each received in a respective bore 25*a*, 25*b* in the lower member 17. As indicated at 27, each bore 25*a*, 25*b* has an inwardly extending flange of somewhat smaller diameter than the remainder of the bore, with the diameter of the flange 27 being only somewhat larger than the diameter of the stabilizing posts 23*a*, 23*b*. Further, at the distal end of each of the stabilizing posts, an enlarged head 29 is provided with the head being somewhat larger than the diameter of the post and being somewhat larger than the bore in flange 27. In this manner, with the posts received in their respective bores, the heads 29 on the end of each post cooperates with flange 27 so as to prevent the body members 19 and 21 from becoming distracted (moved apart) more than a predetermined distance. As best shown in FIG. 17, each of the stabilizing posts 23*a*, 23*b* may have an optional longitudinal slot 30 which enables the post to be somewhat resiliently compressed so that the flanges 29 on the ends of the posts may be inserted through the bores thus allowing the posts to be received in their respective bores 25a, 25b. Once the posts have been inserted in the bores, the posts will spring back to resume their shape and size prior to being compressed. It will be further understood that the bodies of posts 23a, 23b preferably have a sliding close fit within the bores of their respective flanges 27 such that the posts stabilize the upper and lower body members relative to one another so as to resist the body members from twisting, shearing, or tipping relative to one another in all directions. These stabilizing posts help maintain the body members 17 and 19 oriented in a desired parallel relation to one another as the implant 1 is inserted within the disc space DS and distracted, in the manner as will be hereinafter described. Further, the provision of flanges 27 and 29 provide a tactile feel that prevents over distraction of the body members 17 and 19. While the above-described stabilizing posts 23a, 23b have been described as having slots 30 therein, it will be understood that the slots may be omitted and that the posts may be solid members.

Figure 18:
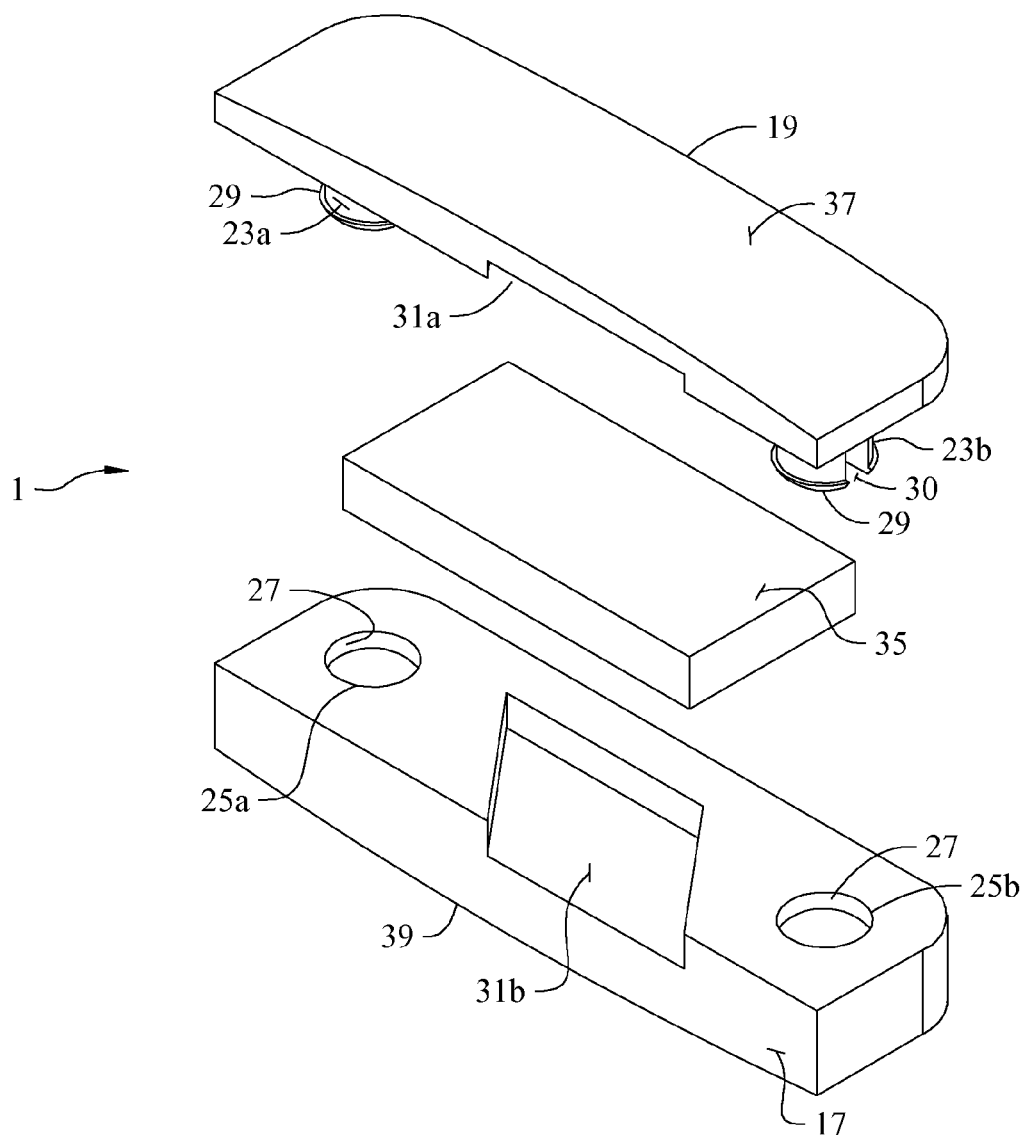
FIG. 18 is a top perspective exploded view of the implant.

As perhaps best shown in FIG. 18, each of the body members 17 and 19 has a respective oblique or angled slot 31a, 31b formed in its inner face. When the body members are assembled as shown in FIG. 13 and with the implant 1 installed as described above with the implant bearing on the cortical rims CR of the vertebrae bodies, the slots 31a, 31b are oriented so as to be generally in alignment with incision 11 in annulus 9 so to allow the blades of a distractor instrument to be inserted in line into these slots. With the operating blades of the distractor received in slots 31a, 31b, the distractor may then be operated so as to distract the body members 17 and 19 and so as to simultaneously distract the vertebrae bodies on opposite sides of the disc space DS a desired amount. The parallel distractor is used to expand the space 21 between the body members 17 and 19 using preoperative imagining and intraoperative tactile feedback of annular and ligamentous tensioning. Of course, when spacer 35 of the proper predetermined thickness is inserted in space 21, the desired amount of distraction is maintained. It will be appreciated that the angled slots 31a, 31b are substantially centered with respect to implant 1 so as to balance the distraction loading and so as to minimize binding of the stabilizing posts 23a, 23b within the openings of flanges 27 upon distraction and retraction of the body members relative to one another.

A spacer 35 of predetermined thickness is insertable within the space 21 between body members 17 and 19 once the disc space DS and the body members 17 and 19 of implant 1 have been distracted the desired amount. In accordance with this disclosure, a series of spacers 35 of predetermined thicknesses may be provided so that, depending on the amount of distraction needed, and depending on the disc space and the anatomical characteristics of the patient, a spacer is provided for the amount of distraction required. For example, spacers 35 may be provided in predetermined thicknesses of, for example, 1 mm, 2 mm, or 3 mm. The shape and size of spacers 35 distribute the anatomical spinal loads over a relatively wide surface area of the upper and lower body members 17, 19. The geometry of slots 31a, 31b facilitates easy withdrawal of the distractor instrument after shim or spacer 35 has been properly positioned between the implant members 17 and 19. Of course, it will be recognized that the distractor instrument may be used for final positioning and placement of implant 1 within the disc space.

As shown in FIG. 4, the length of implant 1 is sufficient so as to span the disc space DS anteriorly, and to bear on the cortical rims CR of the vertebrae bodies. The upper face 37 of upper body 19 and the lower face 39 of lower body 17 are preferably of a convex shape so as to generally conform anatomically to the disc space contacting the vertebrae endplates. This anatomic fit of the implant relative to the adjacent vertebrae in addition to the load sharing with the cortical rims of the vertebral bodies will maximize the load bearing capability of the implant. The outer faces 37 and 39 of body members 19 and 17 may be appropriately textured so as to prevent migration of the implant relative to the vertebrae. Still further, the outer anterior ends of the lower and upper body members are radiused, as indicated at 41, so as to generally conform to annulus 9 when the implant is positioned bilaterally within the disc space DS with the outer ends of the implant in bearing engagement with the hard cortical rims CR of the upper and lower vertebrae bodies. It will be noted that, as shown in FIG. 4, the ends of implant 1 may protrude somewhat through the annulotomies or openings 15a, 15b in the annulus 9. However, it will be understood that the anterior ends 41 of the lower and upper body members may be shaped to generally conform to the shape of the disc space DS so that they do not substantially project out beyond the outer surfaces of the vertebrae bodies. Of course, if the lower and upper body members are so shaped to better conform to the vertebrae bodies and to reduce the protrusion of the ends of the body members out beyond the disc 3, the ends of spacer 35 would be similarly shaped.

After the implant has been inserted in the disc space DS and oriented and positioned as above described with the ends of the implant supported by the cortical rims CR of the upper and lower vertebrae bodies and after the implant has been distracted as described and the desired thickness spacer 35 has been inserted between the lower and upper bodies 17 and 19, bone graft material may be packed between the implant and the posterior annulus filling the disc space. It will also be understood that vertebrae fixation will be used in conjunction with implant 1. The fixation system used in conjunction with implant 1 is conventional and no particular system is preferred. It will be understood that as the bone graft material grows within and substantially fills the disc space DS, the vertebrae will be fused by this bone growth.

Figure 6:
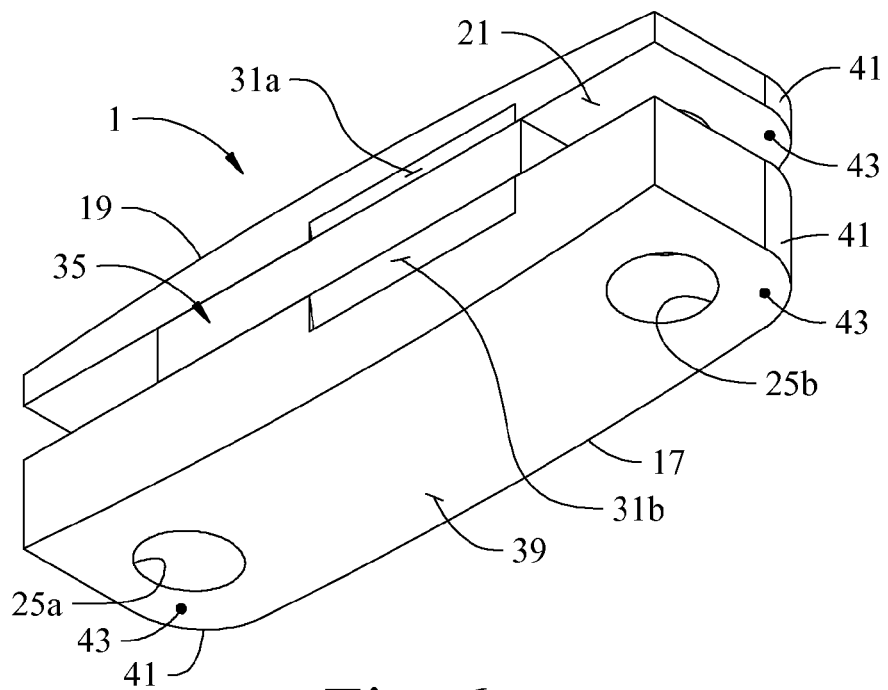
FIG. 6 is a posterior perspective view of the implant shown in FIG. 5, as viewed from below.
Figure 7:
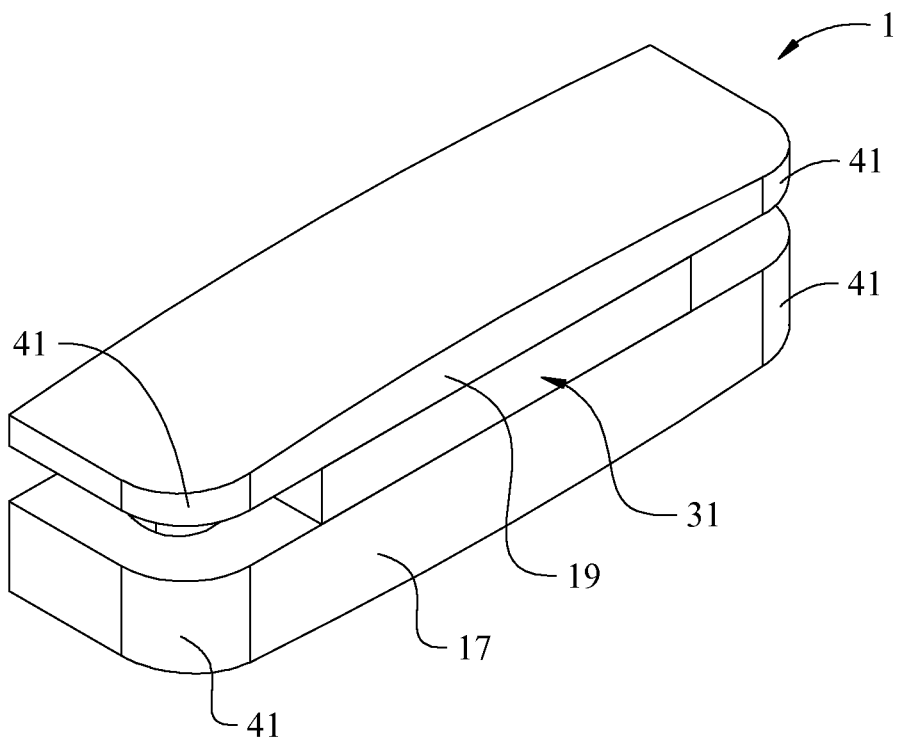
FIG. 7 is an anterior perspective view of the implant shown in FIG. 6, as viewed from above.
Figure 8:
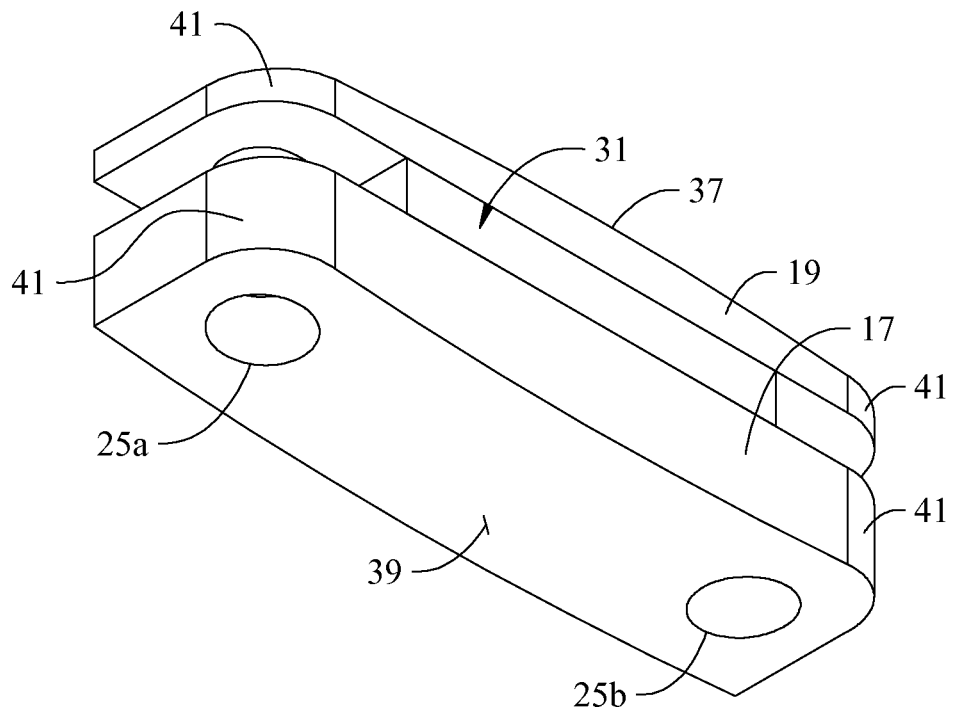
FIG. 8 is another anterior perspective view of the implant, as viewed from below.
Figure 9:
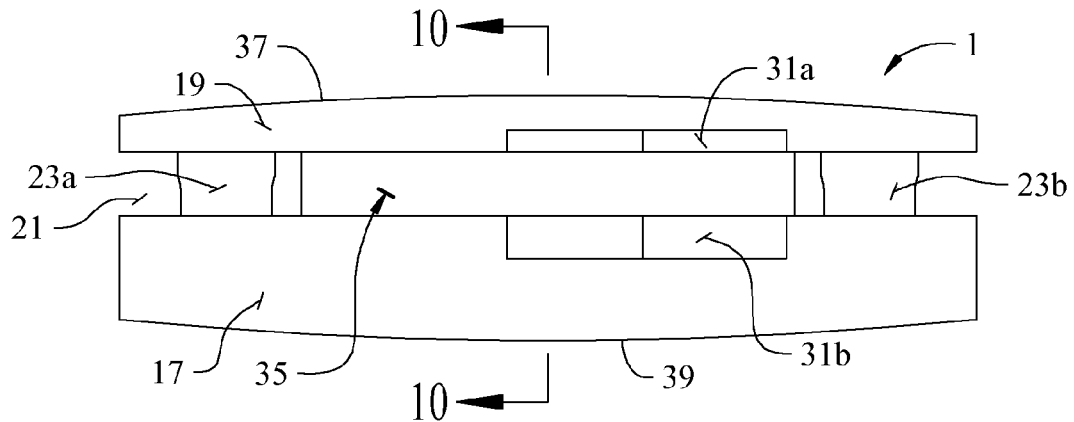
FIG. 9 is a posterior elevational view of the implant illustrating oblique slots in the inner faces of the upper and lower body members with a spacer inserted between the inner faces of the upper and lower body members.
Figure 10:
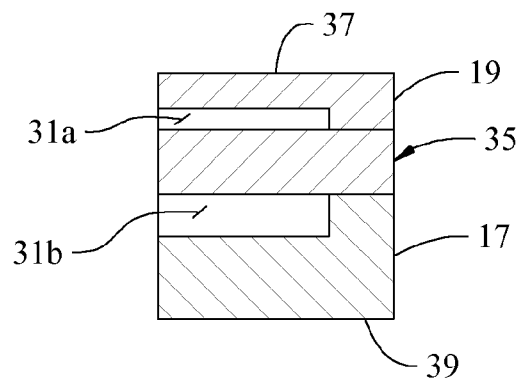
FIG. 10 is a vertical cross sectional view of the implant taken along line 10-10 of FIG. 9.
Figure 11:
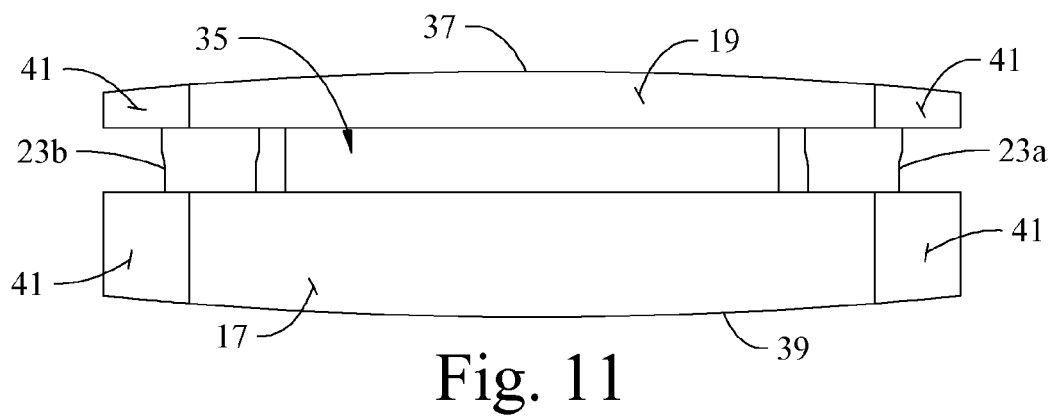
FIG. 11 is anterior view of the implant shown in FIG. 9.
Figure 12:
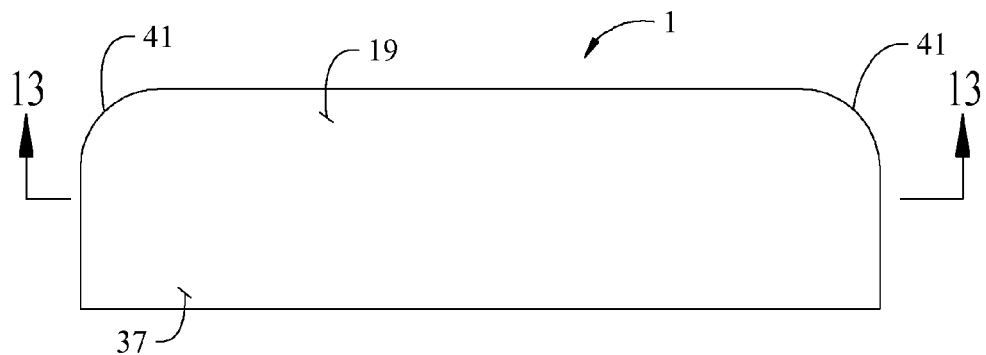
FIG. 12 is a top plan view of the implant.

It will be understood that the lower and upper bodies 17 and 19 of implant 1 and spacer 35 may be made of any suitable material such as surgical stainless steel, titanium, polyetheretherketone (PEEK), or carbon fiber reinforced PEEK, other surgical grade polymer or other material. Of course, the implant 1 and the spacers are delivered to the operating room in a sterile condition, and are available in a variety of lengths and profiles to as optimize patient fit. It may be preferable that implant 1 be made of PEEK because the modulus of elasticity of PEEK is similar to the modulus of elasticity of bone. However, PEEK is substantially radiolucent and thus is not readily viewable in radiographs. If PEEK is used for the implant, it is preferable that radio opaque markers, as indicated at 43 (as shown in FIGS. 5 and 6), be inserted within the implant so that the position and orientation of the implant may be fluoroscopically verified once the implant has been inserted in the disc space DS. Preferably, markers 43 are made of tantalum or other suitable metal so as to show more clearly on radiographic images.

With implant 1 properly positioned between the vertebrae, with the implant properly distracted, with spacer 35 of the proper thickness inserted between body members 17 and 19, and with the afore-mentioned bone graft material packed between the implant and the posterior annulus, conventional posterior spinal fixation appliances (not shown), such as pedicle screws, are applied. Compression is applied to the entire construct so as to restore or maintain sagittal alignment, so as to fixate the structural implant 1 within the disc space DS between adjacent vertebrae, and so as to provide the optimal environment for bone fusion of the vertebrae.

Referring now to FIGS. 19-41, a second embodiment of the implant of this disclosure is indicated in its entirety by reference character 101. The "primed" reference characters shown in FIGS. 19-30 ranging between 1 and 43 indicate parts having substantially the same construction and function as the parts identified by these reference characters 1-43 in FIGS. 1-18. However, some of these components have been modified to carry out a somewhat different function, as will be described.

Figure 19:
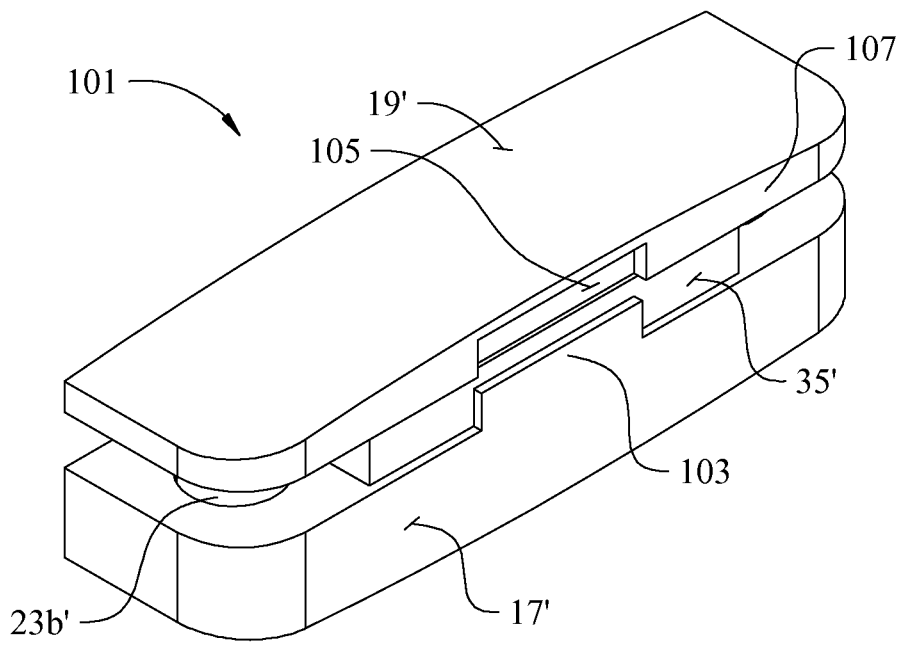
FIG. 19 is an anterior perspective view of a second embodiment of the implant of the present disclosure illustrating a tab extending upwardly from the anterior end of the lower body member with the tab being adapted to fit within a corresponding recess in the anterior face of the upper member so that upon distraction of the space between the body members and with a spacer disposed within the space between the upper and lower body member, the tab prevents anterior displacement of the spacer from between the body members.
Figure 20:
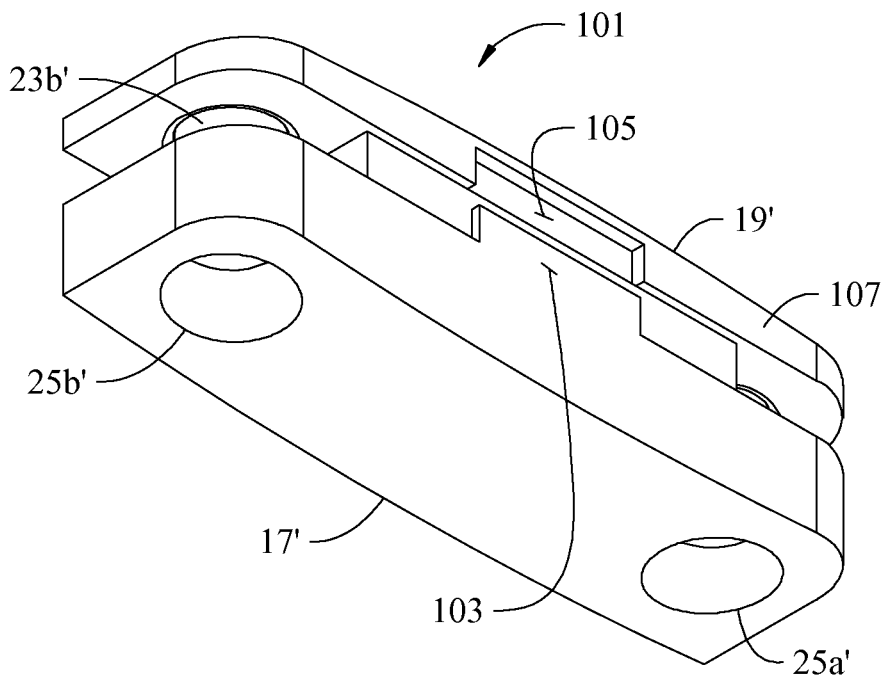
FIG. 20 is a bottom perspective view of the implant shown in FIG. 19.

As shown in FIG. 19, lower body member 17' has a tab 103 extending upwardly from the inner surface of one of the body members, for example, the lower body member along the anterior end thereof. This tab 103 extends up from the upper surface of the lower body member a distance sufficient so as to be at least partially slidingly received in a corresponding groove 105 formed in the anterior wall 107 of the other body member, for example, upper body member 19' when a spacer 35' is received within space 21' between the upper and lower body members and when the upper and lower body members are at least partially retracted with spacer 35' disposed therebetween. In this manner, tab 103 prevents movement of the spacer beyond the anterior end of the body members and thus self-locates the spacer in anterior/posterior direction. The tab further prevents anterior migration of the spacer 35' beyond the anterior edge of lower body member 17' during normal use of the implant by the patient. While tab 103 is shown to be an elongate single tab extending along the anterior edge of the spacer 35', it will be understood that the tab may actually be two or more spaced tabs extending upwardly from the spacer.

Figure 21:
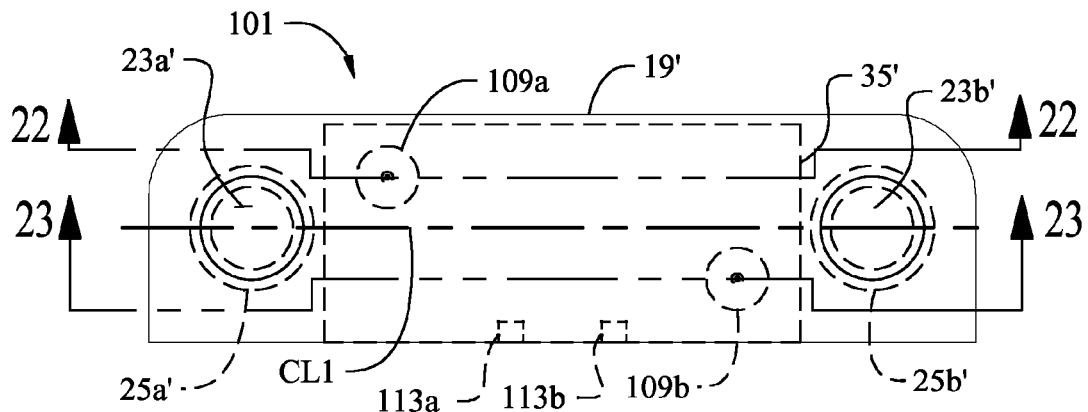
FIG. 21 is a top plan view of the implant shown in FIGS. 19 and 20, with a spacer (shown in dotted lines) positioned between the upper and lower body members.
Figure 22:
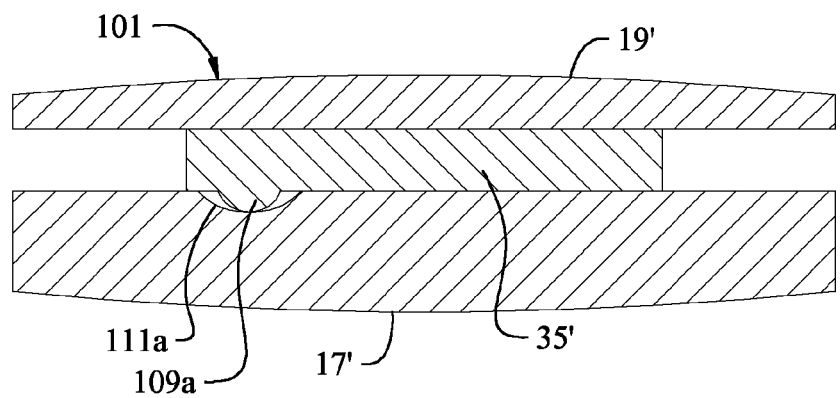
FIG. 22 is a vertical section view taken along line 22-22 of FIG. 21 illustrating a first or anterior detent protuberance projecting downwardly from the bottom face of the spacer with this first detent protuberance being received in a corresponding first enlarged recess in the top face of the lower body so as to aid in locating the spacer relative to the lower body member and so as to prevent displacement of the spacer relative to the lower body member upon retraction of the space between the upper and lower body members and upon application of compression and in normal use.
Figure 23:
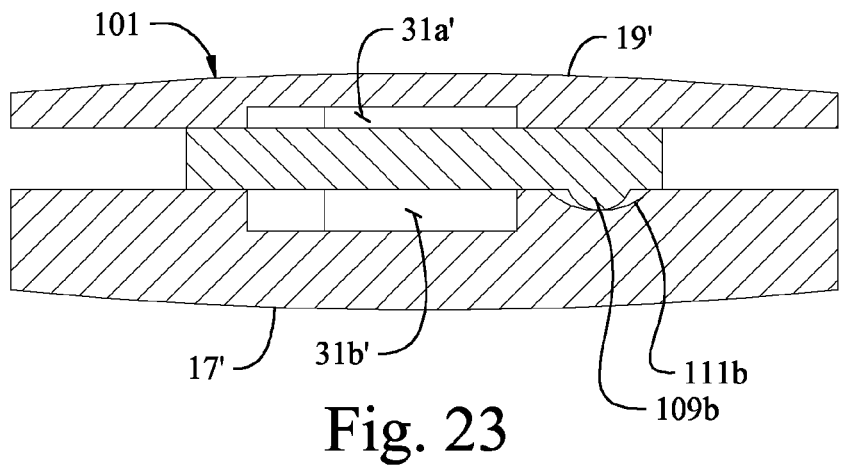
FIG. 23 is a vertical section view taken along line 23-23 of FIG. 21 illustrating a second or posterior detent protuberance projecting downwardly from the bottom face of the spacer with this second detent protuberance being received in a corresponding second enlarged recess in the top face of the lower body so as to aid in locating the spacer relative to the lower body member and so as to prevent displacement of the spacer relative to the lower body member upon compression of the space between the upper and lower body members.
Figure 24:
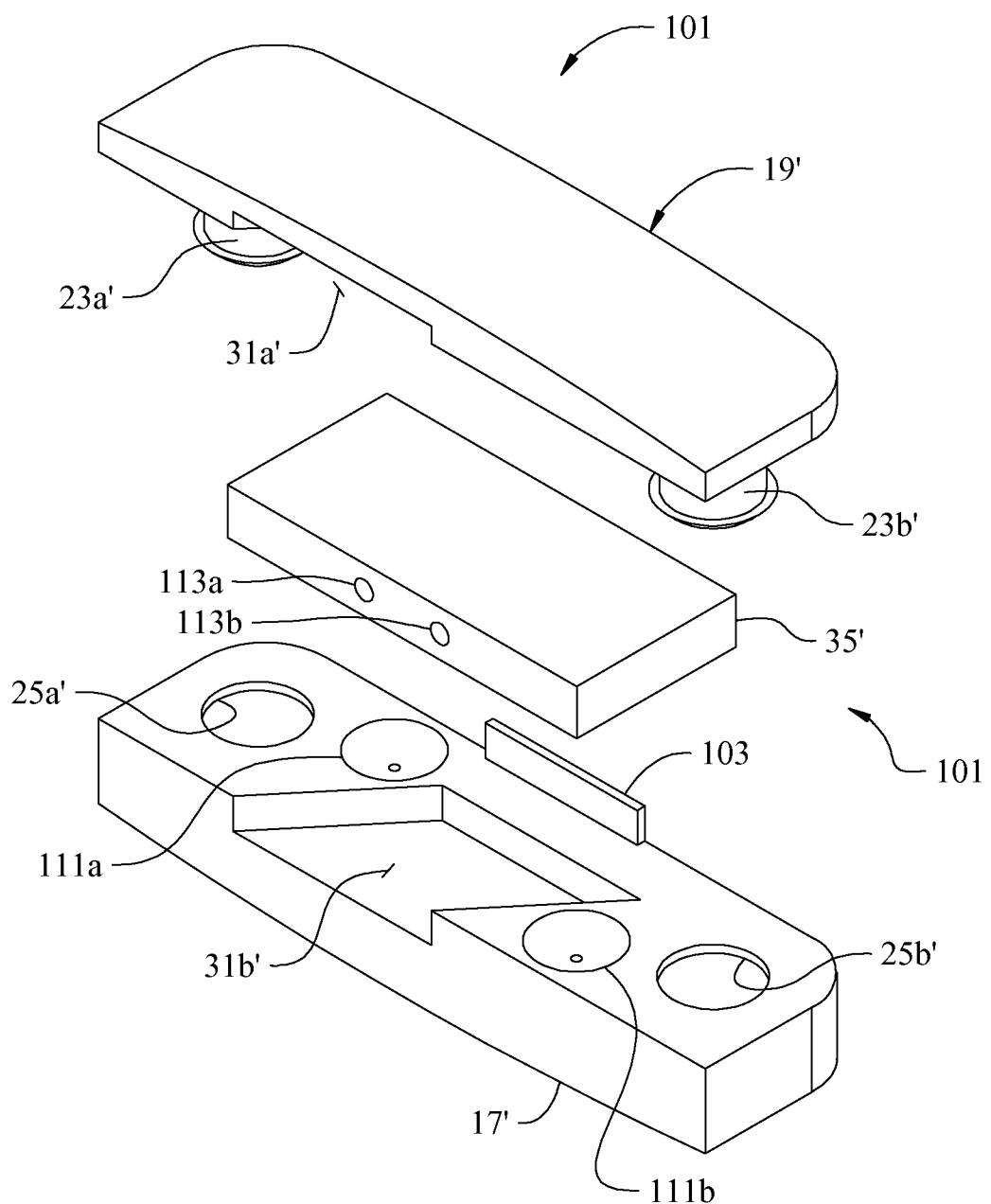
FIG. 24 is an exploded perspective view of the implant shown in FIGS. 19-23, as viewed from above.
Figure 25:
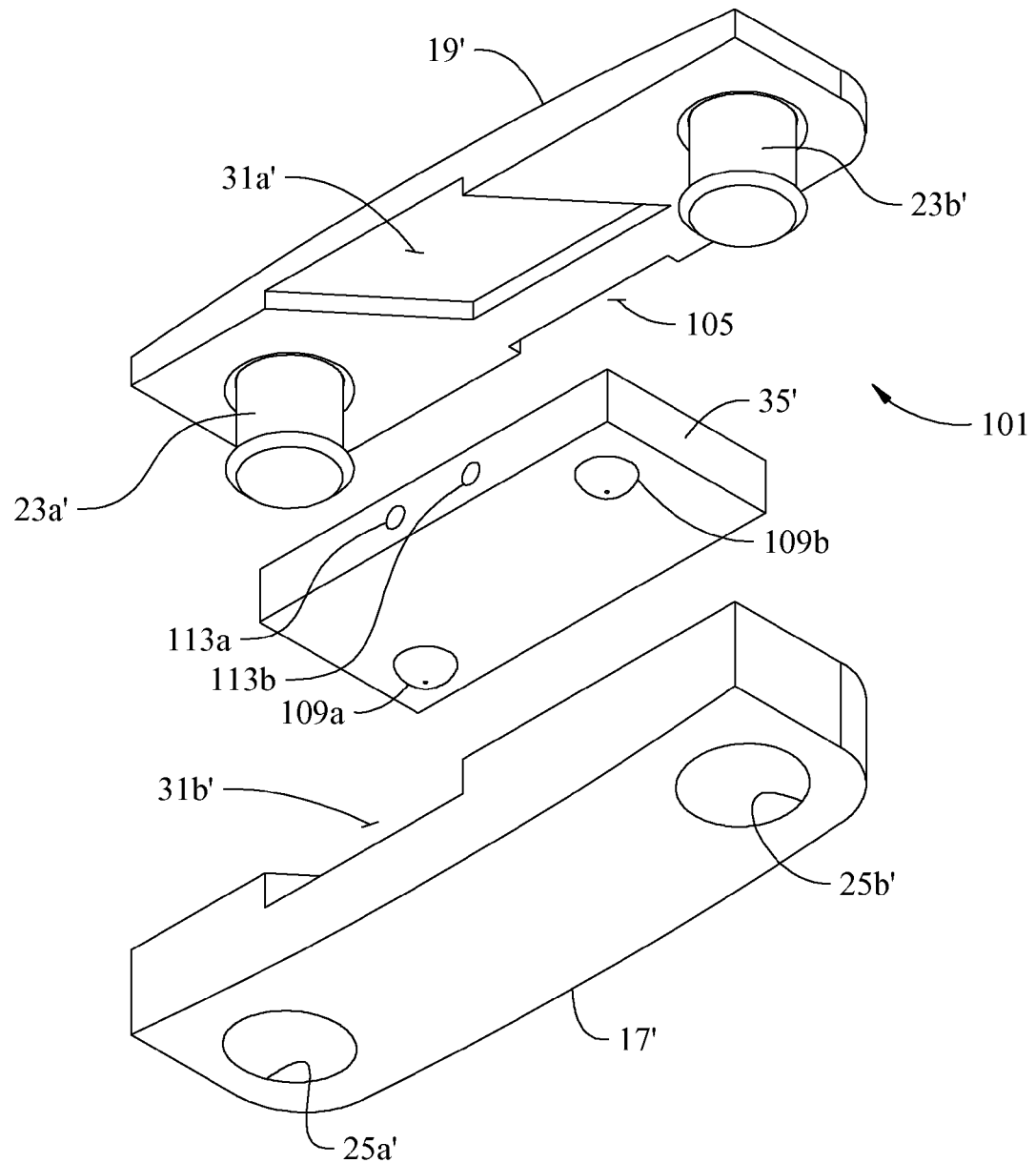
FIG. 25 is an exploded perspective view of the implant shown in FIGS. 19-24, as viewed from below, illustrating a pair of spaced detent protuberances on the bottom face of the spacer.
Figure 26:
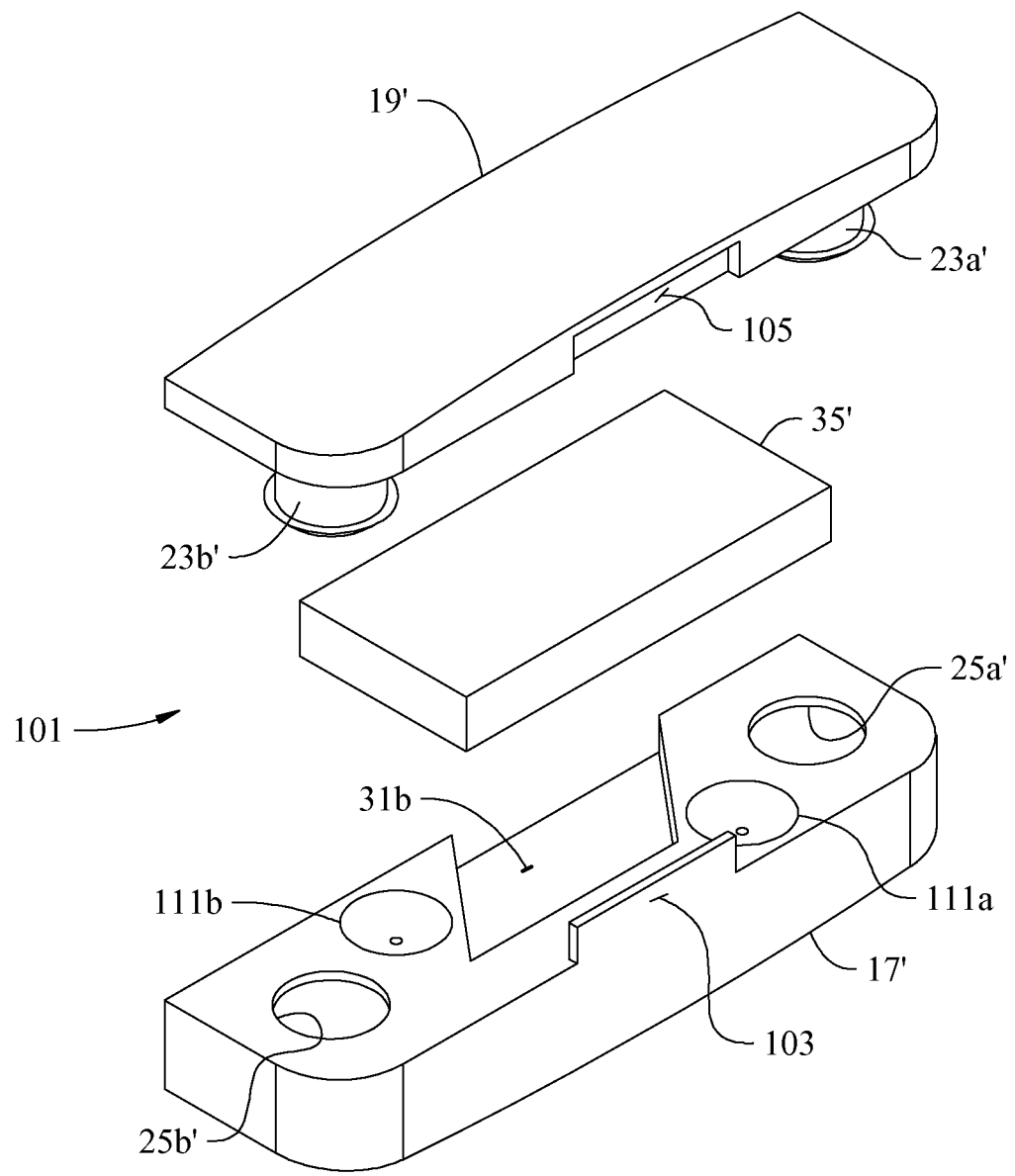
FIG. 26 is an anterior exploded perspective view, as viewed from above, of the implant illustrating the location of the first and second protuberance receiving recesses formed in the upper face of the lower body, as these recesses are positioned relative to the diagonal slot provided in the lower body for receiving the lower blade of a parallel distractor used to expand the space between the upper and lower body members.
Figure 27:
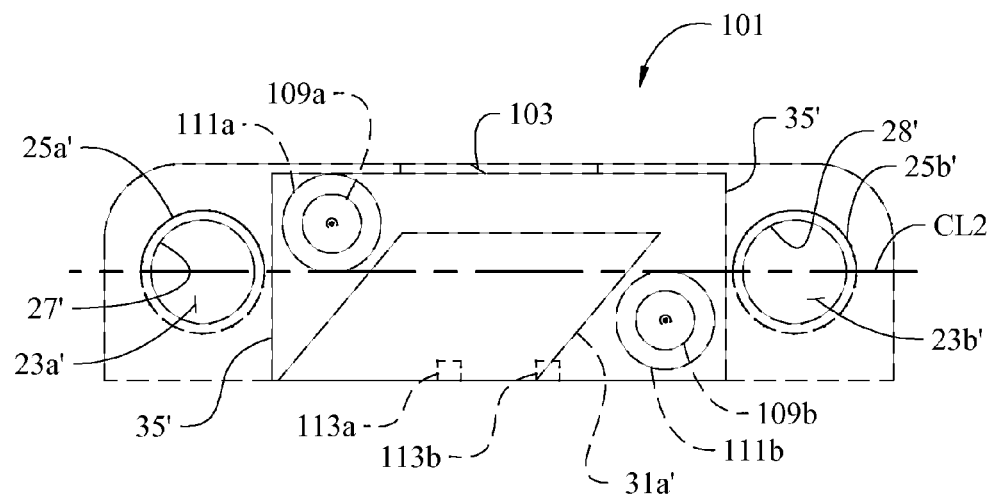
FIG. 27 is a top plan view of the lower implant body member shown in FIGS. 19-26 in which the spacer is substantially centered between the stabilizing posts and in which the anterior and posterior detent protuberances (as shown in dotted lines) are substantially centered relative to their respective recesses (also shown in dotted lines)

Referring now to FIGS. 21-30, the bottom face of spacer 35' is shown to have a pair of downwardly projecting male protuberances, as indicated at 109a, 109b. Each of these protuberances has a generally part-spherical convex outer surface for purposes as will be described. Further, the upper surface of lower body member 17' has a corresponding pair of female recesses, as indicated at 111a, 111b, positioned to receive a respective protuberance. Each of these female recesses has a generally part-spherical concave surface that is engaged by its respective male protuberance. As shown best in FIGS. 22-28, each recess 111a, 111b is larger in diameter than its respective protuberances 109a, 109b for purposes as will appear. As shown in FIG. 24, recesses 111a, 111b are spaced on opposite sides of slot 31b' in areas of the upper surface of lower body member 17' large enough to accommodate the recesses. As further shown in FIG. 21, protuberances 109a, 109b are preferably spaced on opposite sides of a first centerline CL1 (as shown in FIG. 21) of spacer 35' an equidistant amount. The respective recesses 111a, 111b are also preferably equidistantly spaced on opposite side of a second centerline CL2 (as shown in FIG. 27) diametrically extending through bores 25a', 25b' in lower body member 17'. However, those skilled in the art will recognize that the location of the protuberances and the recesses may be at any desired location. It will be further understood that while two protuberances and two recesses are shown, that other numbers of and shapes of the protuberances and recesses may be utilized.

It will be appreciated by those skilled in the art that instead of protuberances 109a, 109b being provided on the bottom face of spacer 35', they may instead (or may in addition) be provided on the upper face of the spacer and the recesses 111a, 111b may be provided on the lower face of the upper body member 19'. Further, it will be understood that the recesses may be provided on the spacer and the protuberances may be provided on a cooperating inner face of an adjacent body member.

It will also be appreciated that because recesses 111a, 111b are of larger diameter than their respective protuberance 109a, 109b, and because the generally part-spherical surfaces of the convex male protuberances engage the generally part-spherical female concave surfaces of their respective recesses, the mating convex surface of the protuberance acts like a cam follower and concave surfaces of the recesses act as a cam so that upon the application of compressive loads to the implant 101, the cooperating and complimentary protuberances and recesses will guide or force the protuberances to move downwardly toward the bottom of the concave recesses so as to self-position and/or to self-center the spacer relative to the body members. While the shape of the protuberances are recesses have been described as being preferably part-spherical, it will be understood that, in accordance with this disclosure, that other rounded shapes may be employed.

In use, as the distractor instrument (not shown) is withdrawn from slots 31a', 31b', as the disc space DS is retracted, and as compression is applied to the spinal column, this compression will tend to effect the above-described camming action that will self center (or self-align) the spacer 35' in proper position within the space 21' between the upper and lower body members 19' and 17'. Further, with such compression loads applied to implant 101, protuberances 109a, 109b will interfere with (bear against) the sides of the recesses 111a, 111b thereby to securely hold or retain spacer 35' in its desired position within space 21'. Further, the complimentary protuberances and recesses, when under compression loading, cooperate with one another so as to resist migration of the spacer relative to the body members during normal use by the patient. It will also be appreciated that the height of the protuberances and the depth of the recesses are such that with the protuberances received within their respective recesses, the protuberances may carry at least some of the compression load applied to spacer 35' by the upper and lower body members 17', 19' of implant 101. Still further, with the protuberances 109a, 109b positioned in the bottom of their respective recesses 111a, 111b, respectively, the protuberances and the recesses prevent or resist movement (migration) and pull-out of the spacer relative to the body members 17', 19' in all directions. Also, the posts 23a, 23b will prevent lateral displacement of the spacer within the implant 101.

Figure 28:
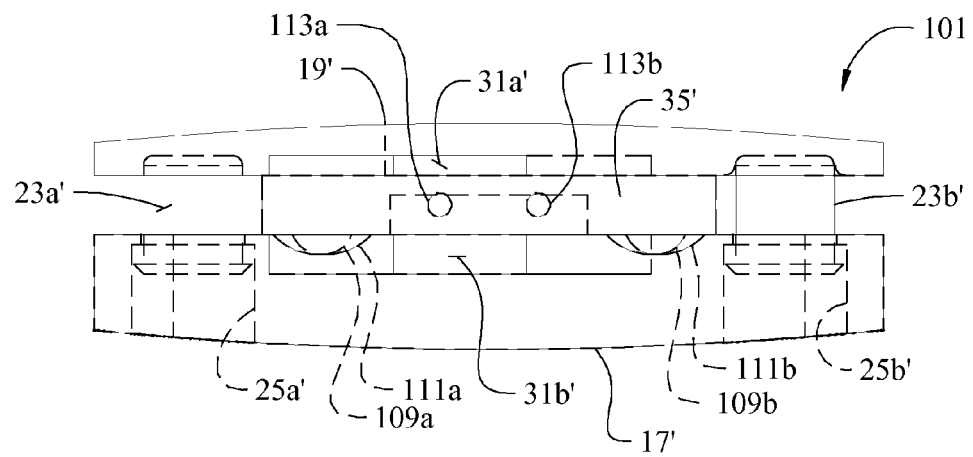
FIG. 28 is a posterior side elevational view of the implant shown in FIG. 27 with the space between the upper and lower body members distracted and with a spacer interposed between the upper and lower body members with the lateral ends of the spacer substantially centered between the stabilizing posts.

It will be further noted in FIGS. 27 and 28 that with the spacer in its desired position, the protuberances 109a, 109b are substantially centered relative to their respective recesses 111a, 111b so that spacer 35' is substantially centered between posts 23a' 23b'. It will be appreciated that so long as each of said protuberances are received anywhere within its respective recess, spacer 35' will be properly positioned in a desired general location between body members 17', 19'. It will be understood that with each of the protuberances substantially centered with respect to its respective recess, that the spacer will be located or positioned in a nominal position relative to the body members, as illustrated in FIGS. 27 and 28.

Further, it will be noted that the anterior end of the spacer 35' abuts against (or is in relatively close proximity to) the inner or posterior face of tab 103. In this manner, tab 103 cooperates with the anterior face of spacer 35' to as to prevent anterior displacement of the spacer from its desired general position between the body members 17', 19'. Because of the interaction of the generally convex surfaces of the protuberances and the concave surfaces of their respective recesses, spacer 35' is effectively constrained against anterior, posterior, lateral, and angled movement relative to the upper and lower body members.

Further, as previously described, bone graft material (not shown) is typically packed between the posterior face of implant 101 and the inner face of the posterior annulus substantially filling the disc space DS such that bone graft material also aids in preventing posterior movement of the spacer 35' relative to the body members. Thus, it will be appreciated that tab 103, and the cooperating generally rounded or part-spherical surfaces of protuberances 109a, 109b and recesses 111a, 111b, and the bone graft material prevent migration of the spacer 35' relative to the implant body members 17', 19' not only immediately following surgery, but also during normal use by the patient as the bone graft material fuses the vertebrae together.

Figure 29:
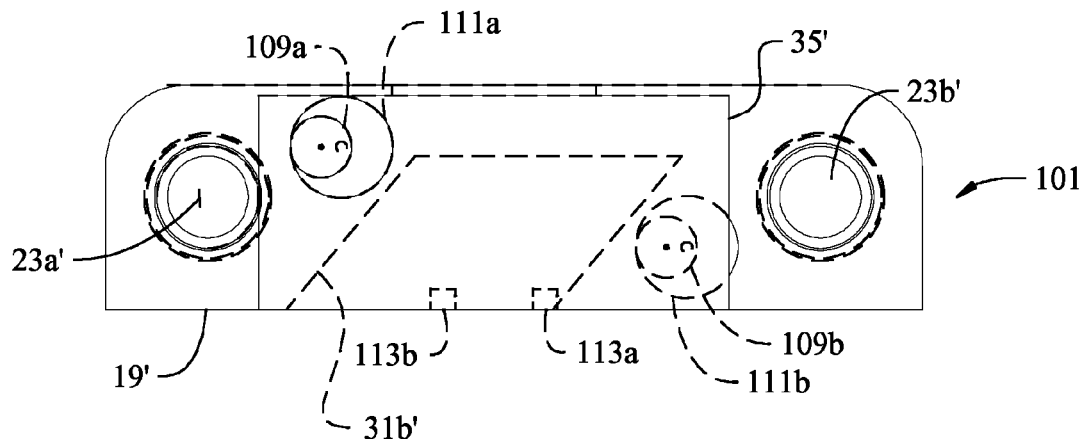
FIG. 29 is a top plan view of the lower implant body with the spacer being offset within the space between the stabilizing posts toward and bearing against the left-hand post such that both the left-hand post and the detent protuberances are received in their respective recess so as to positively prevent lateral movement of the spacer, and such that the protuberances cooperating with their respective recesses positively prevent movement of the spacer relative to the implant bodies.
Figure 30:
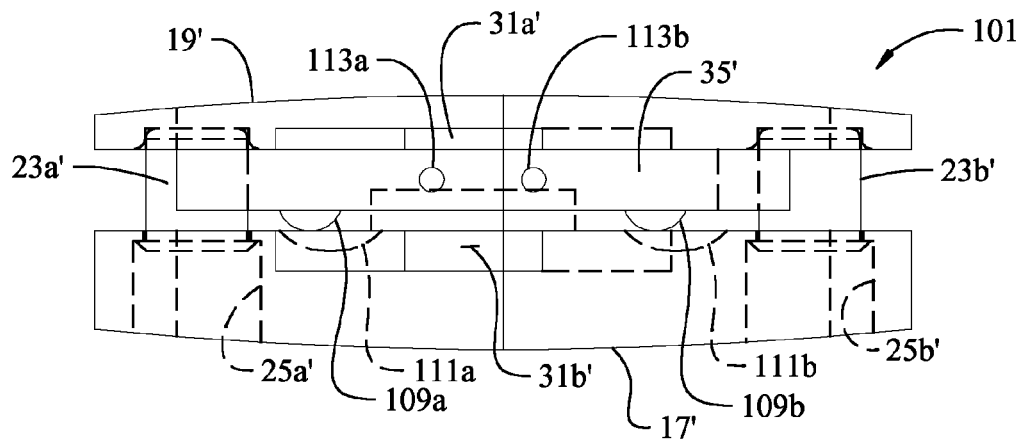
FIG. 30 is a posterior side elevational view of the implant shown in FIG. 29 with the spacer located in the position shown in FIG. 29 with the space between the implant bodies members distracted a distance greater than the thickness of the spacer.
Figure 31:
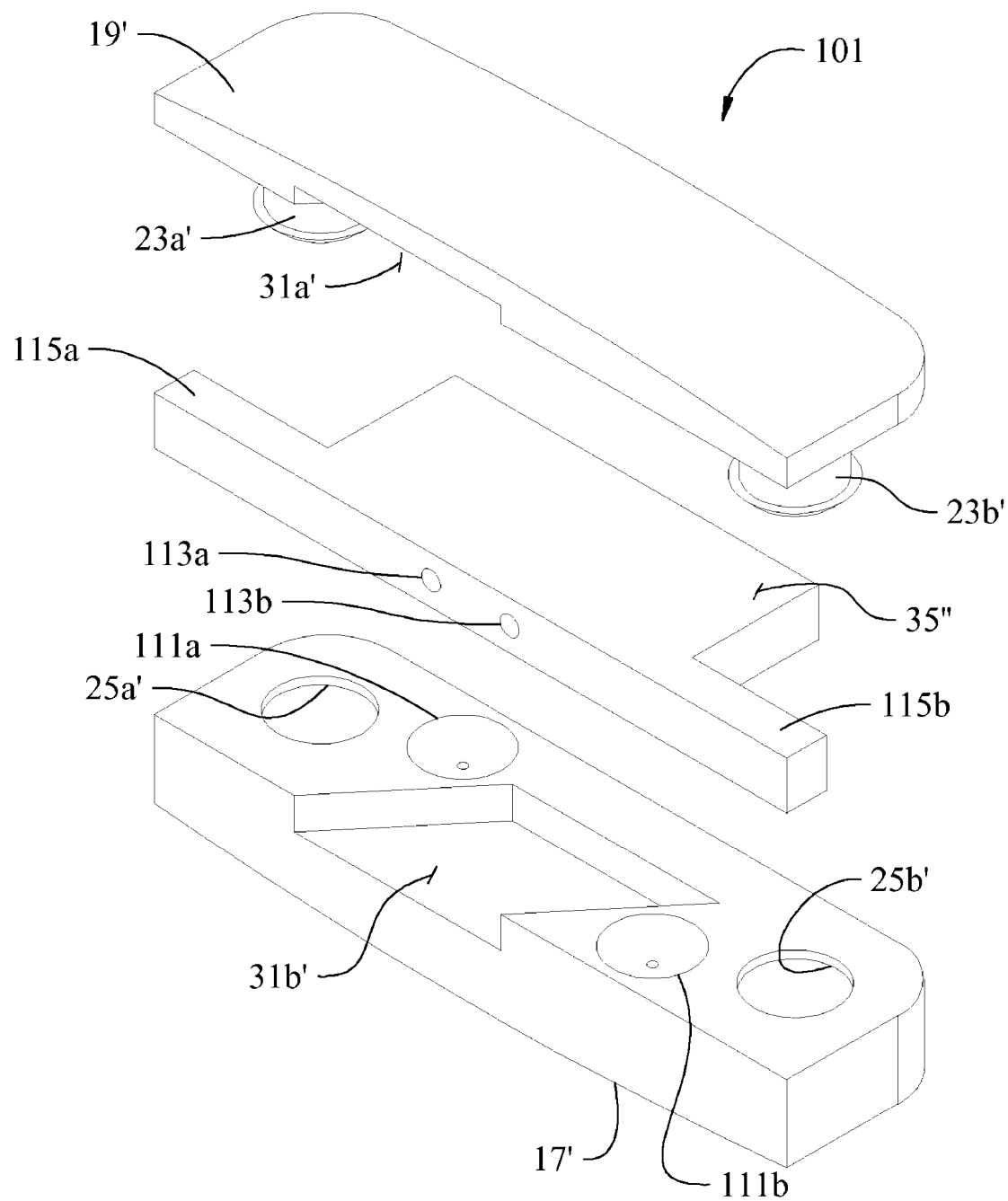
FIG. 31 is an exploded perspective view of the implant having an alternative spacer having a "wing" or extension extending laterally from each posterior side of the spacer for cooperating with the stabilizing posts thereby to prevent anterior movement of the spacer beyond a predetermined location for the spacer between the body members.
Figure 32:
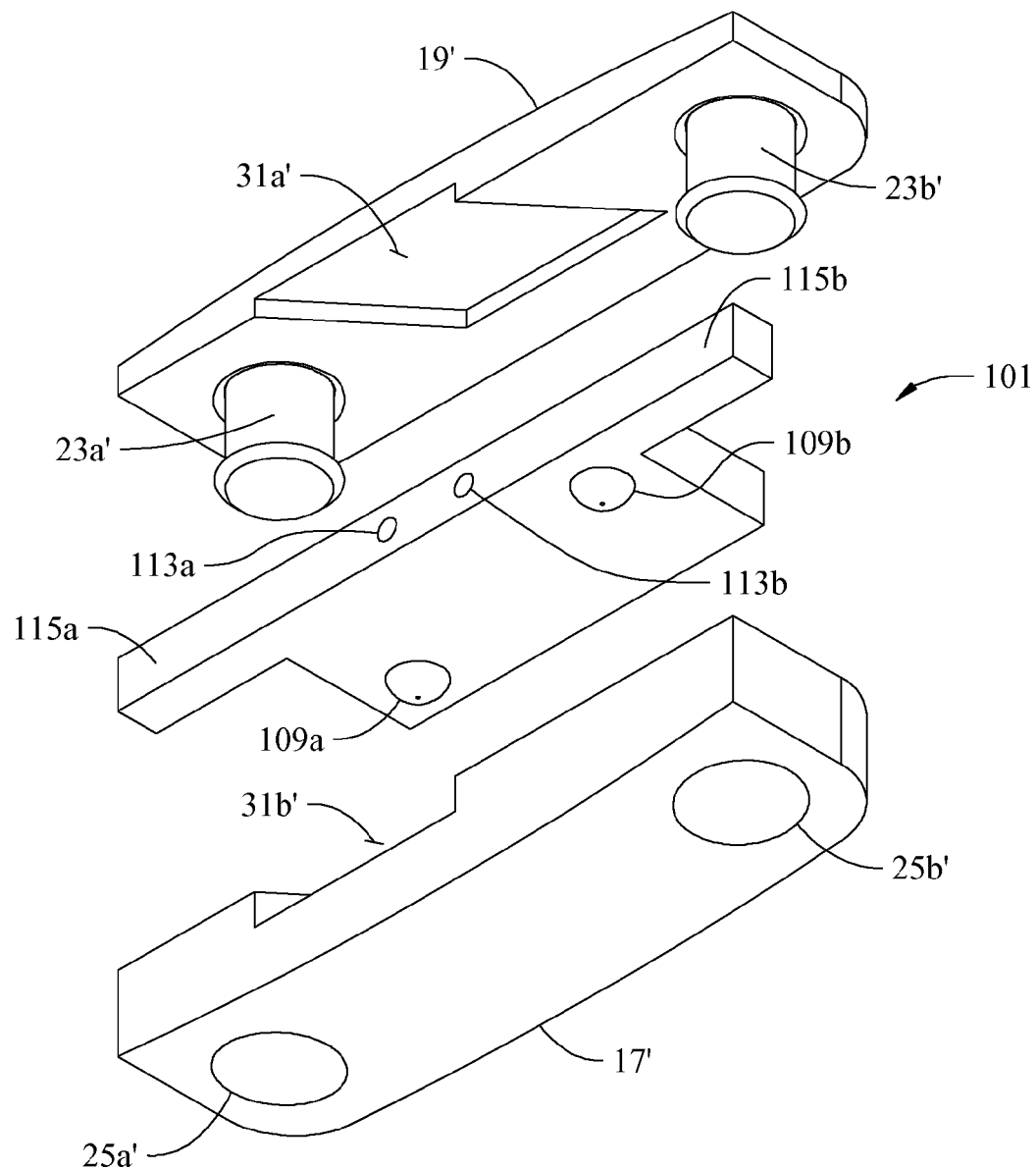
FIG. 32 is a posterior exploded perspective view of the implant and spacer illustrated in FIG. 31.

Referring now to FIGS. 29 and 30, the body members 17' and 19' are shown with spacer 35' laterally offset to the left such that the left end of the spacer is in contact with stabilizing post 23a' and such that the protuberances 109a, 109b are disposed above the extreme left-hand reaches of their respective recesses 111a, 111b. Upon retraction of the disc space DS and upon the application of compression loads to the construct, the previously described camming action of the convex protuberances engaging the concave recesses cause the spacer to move or shift relative to the body members and to be at least partially self-aligned and self-centered with respect to the lower body members so as to be closer to its nominal desired general location, as shown in FIGS. 27 and 29. However, those skilled in the art will recognize that so long as the protuberances are received within their respective recesses, the spacer will be located within its desired general location and that such location results in an acceptable insertion and location of the spacer in implant 101.

This self-centering, self-aligning feature of the spacer 35' means that upon installation of spacer 35' during the surgical procedure, the surgeon need only place the implant 101 within the disc space DS (as described above in regard to implant 1). With the implant 101 so positioned, the surgeon then, using the above-described distractor instrument, distracts body members 17' and 19' and inserts spacer 35' within space 21' between the body members. It will be appreciated that due to tab 103, the stabilizing posts 23a', 23b', and the length of the spacer, the spacer need only be positioned between the posts and somewhat to the posterior of tab 103 such that upon removal of the distractor instrument (which will allow retraction of the vertebrae) and upon the application of a compressive load to the spinal column, the above-described self-centering and self-aligning features of the protuberances 109a, 109b and recesses 111a, 111b will move the spacer from the position as shown in FIGS. 29 and 30 to the substantially centered position of the spacer shown in FIGS. 27 and 28. Of course, if the spacer is shifted to the right, retraction and the application of compressive loads will also self-center and self-align the spacer. Additionally, if there is some angular displacement of the spacer, the protuberances and recesses will straighten the spacer relative to the body members in the same manner.

Further, those skilled in the art will recognize that upon application of compression loads (as herein described) and/or upon the application of repeated micro-motion compressive spinal column loads by the patient, as during sitting or walking, the cooperating protuberances 109a, 109b and recesses 111a, 111b maintain the self-alignment and self-centering of the spacer relative to the upper and lower body members and prevent migration of the spacer relative to the body members.

It will be further appreciated by those skilled in the art that if during the surgical procedure a first spacer is inserted within space 21' between the body members 17' and 19' and if it is determined that the first spacer should be removed, the surgeon need only insert the distractor blades of the distractor instrument (not shown) into slots 31a', 31b' of the body members so as to distract or expand space 21', Then, the first spacer 31' may be readily removed by gripping the spacer with a clamp and removing it from between the body members and to withdraw the spacer through the above-described incision 11 in the annulus 9, as shown in FIG. 4C. Then, a second spacer of, for example, a different thickness, may be readily inserted.

As indicated at 113a, 113b in FIGS. 19-30, a pair of holes is provided in spacer 35' so as to more readily permit the surgeon to grasp the spacer by means of a clamp or other instrument so as to enable the surgeon to maneuver the spacer within space 21' between the body members 17', 19', or to remove the spacer.

It will be further appreciated that with the expandable lumbar interbody or implant 1 of the present disclosure in its collapsed height condition without spacer 35 installed between the upper and lower body members 17, 19, it is easier for the surgeon to insert the interbody into the disc space DS through the annulotomy 11, and the interbody is more readily maneuverable by the surgeon within the disc space so that the interbody spans the apophyseal ring and so that the ends of the interbody are properly inserted in the anterolateral annulotomies 15a. 15b, as generally shown in FIG. 4. It will also be appreciated that with the interbody 1 in its collapsed condition, it is much easier to remove the interbody from the disc space.

Figure 33:
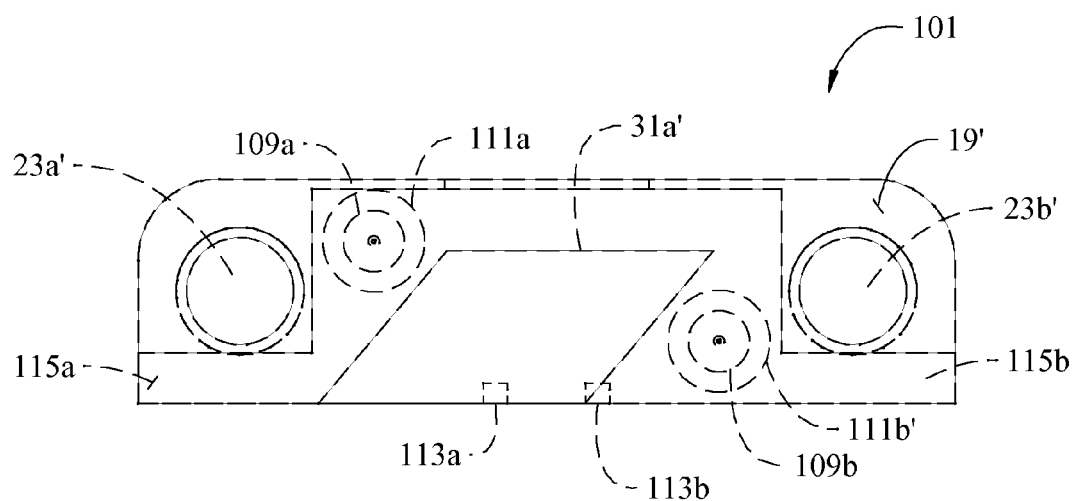
FIG. 33 is a top plan view of the implant shown in FIGS. 31 and 32 with the alternate spacer positioned between the upper and lower body members with the wings or extensions bearing against their respective posts so as to prevent anterior movement of the spacer beyond the position of the spacer shown.
Figure 34:
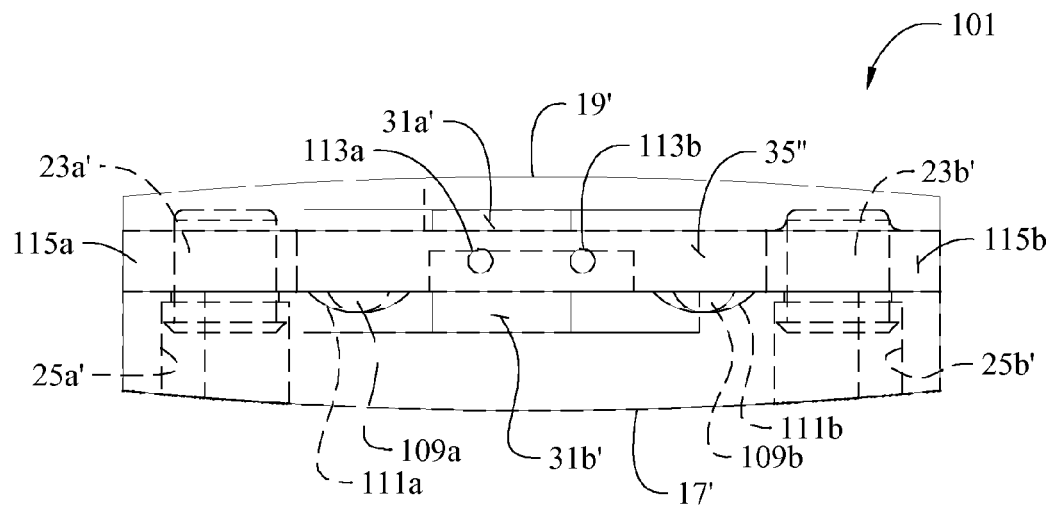
FIG. 34 is a posterior side elevational view of the implant shown in FIG. 33.
Figure 35:
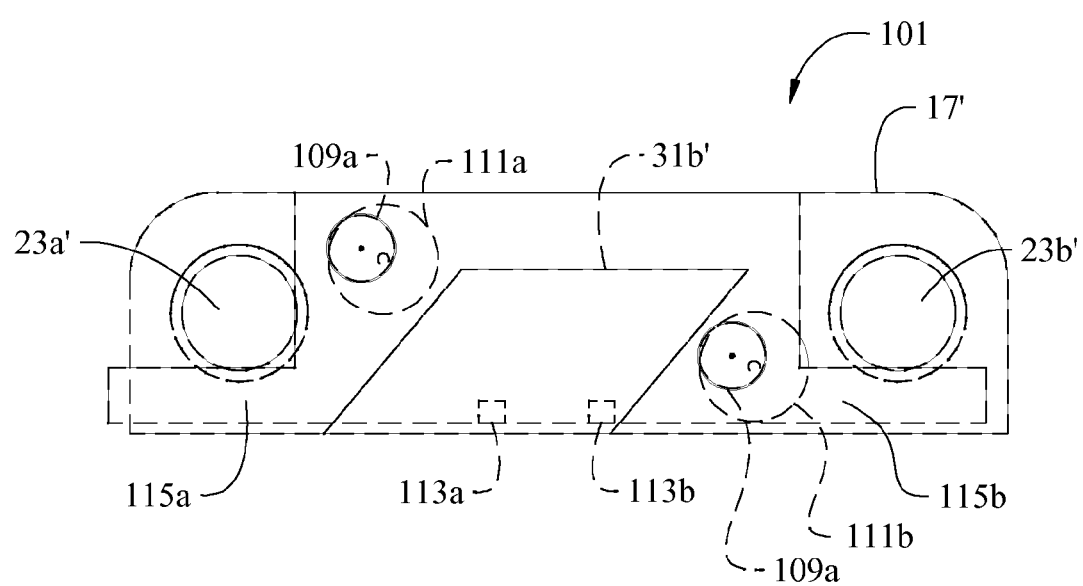
FIG. 35 is a top plan view of the lower body member having the alternate spacer positioned thereon with the left lateral side of the spacer bearing against the left post and with the wings or extensions bearing against the respective posterior faces of their respective posts so as to prevent anterior movement of the spacer relative to the lower body member beyond the position shown.

Referring now to FIGS. 31-35, an alternative embodiment of spacer 35' is shown and is indicated in its entirety at 35". This spacer 35" is shown to have a pair of wings or extensions 115a, 115b, one on each end of the spacer, extending laterally from the posterior side of the spacer. The anterior faces of these wings or extensions bear against the posterior faces of respective posts 23a', 23b' so as to prevent anterior movement of the spacer 35" beyond its predetermined position, as shown in FIGS. 33 and 35. These wings are an alternative structure to or in addition to tab 103 for locating the spacer in anterior/posterior position relative to the body member and for preventing anterior movement of the spacer beyond a desired location. It will be further appreciated that the length of each wing 115a, 115b is such that with the spacer positioned within space 21' (as shown in FIG. 35) such that one lateral side of the spacer bears against its respective post 23a' or 23b', the wing on the opposite lateral side of the spacer still engages the posterior face of its respective post such that both of the wings bear against their respective posts and thus positively prevent insertion of the space in anterior direction beyond a desired anterior position relative to the body members 17', 19'.

Thus, upon installation of the spacer 35", the spacer need only be oriented its protuberances 109a, 109b facing body member 17', with the wings 115a, 115b facing toward the posterior of the implant 101, with the body of the spacer positioned between the posts 23a, 23b'. Then upon retraction of the vertebrae spacing and upon the application of compression loading to the implant 101, the protuberances and the recesses will cooperate, as previously described, so as to self-center and to self-align the spacer relative to the body members. Further, with the protuberances received in their respective recesses and with such normal compression loads applied to the implant, the protuberances and recesses will effectively prevent movement or migration of the spacer relative to the body members. Still further, with bone graft material (not shown) packed within the disc space DS on the posterior side of implant 101, the bone graft material will also aid the protuberances and recesses in preventing movement or migration of the space from between the body members.

Figure 36:
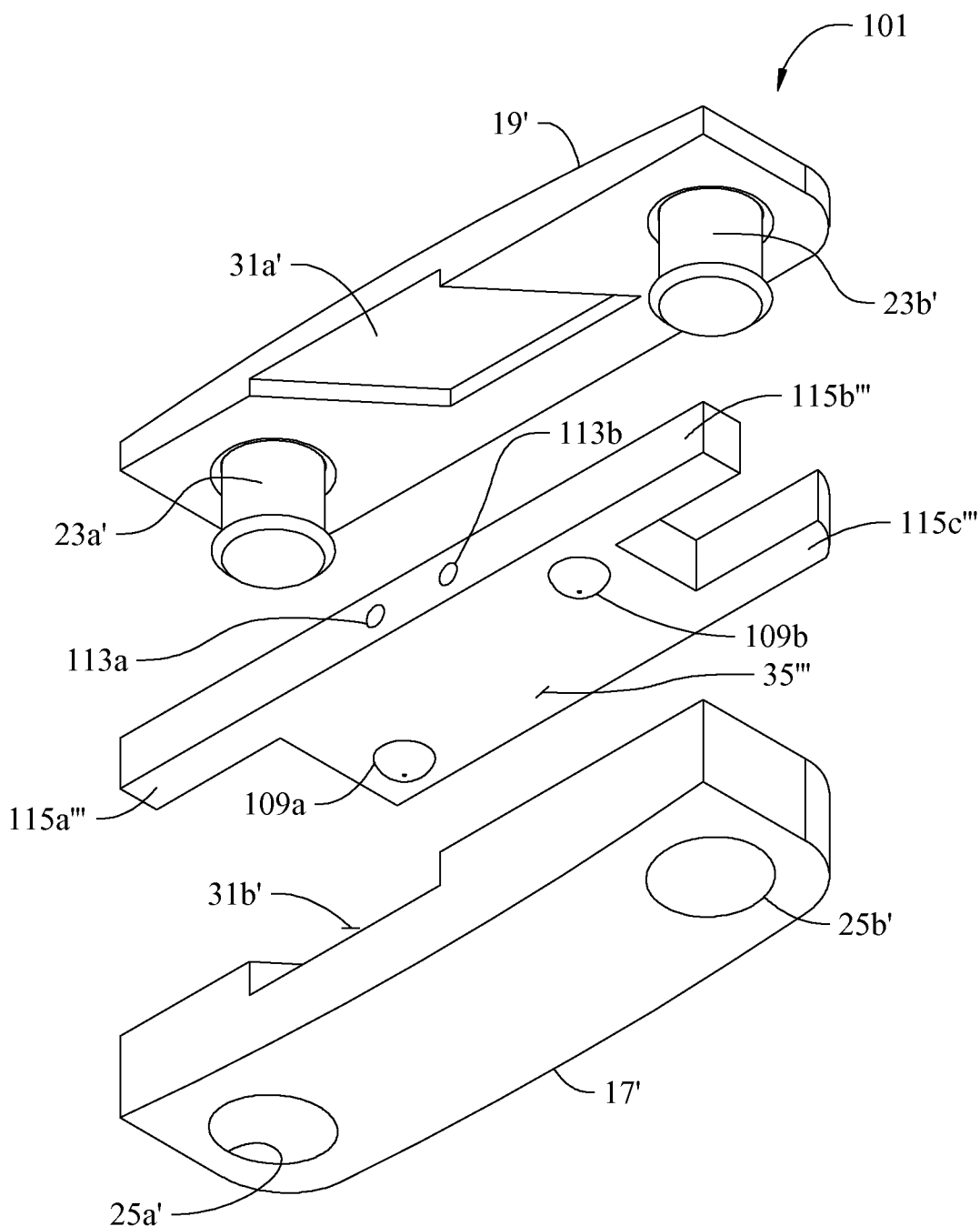
FIG. 36 is a bottom perspective exploded view of still another embodiment the implant similar to that shown in FIGS. 31-35 in which the spacer has a pair of "wings" or tabs on one end and a single "wing" or tab on the other end with the space between the pair of tabs being spaced as to receive a post such that with the spacer inserted between the implant bodies and rotated such that the spacer is substantially parallel to the implant bodies where the posterior tabs prevent anterior movement of the spacer relative to the posts and the anterior tab prevents posterior movement of the spacer.
Figure 37:
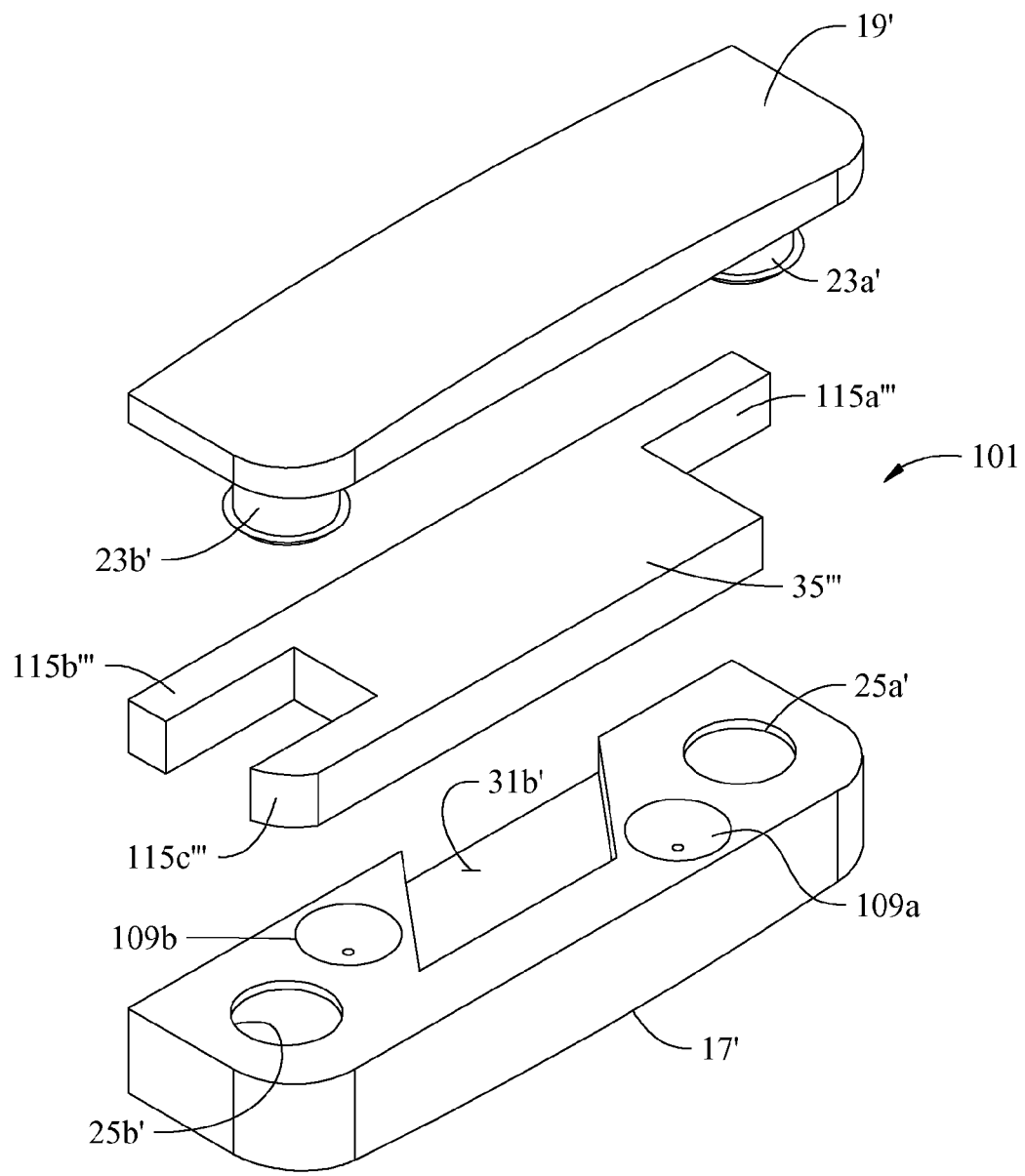
FIG. 37 is a top perspective exploded view of the implant and spacer shown in FIG. 36.
Figure 39:
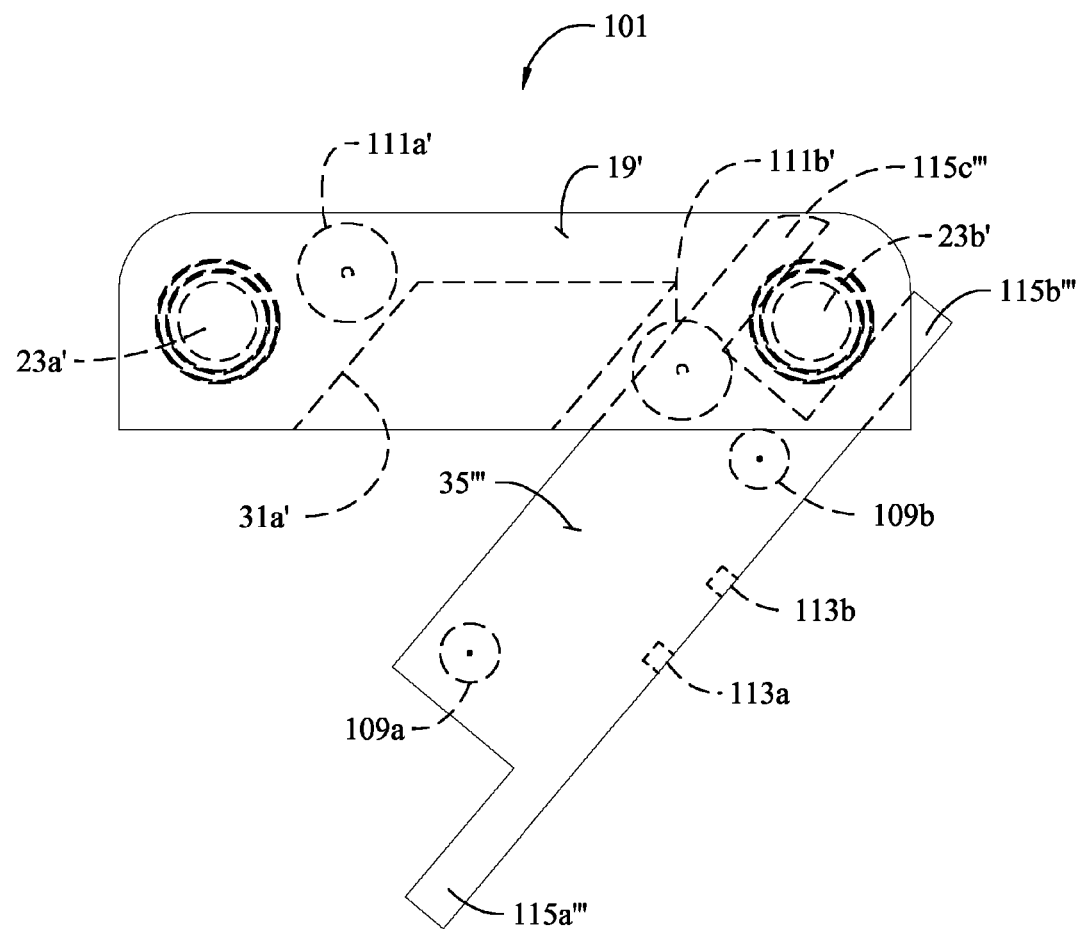
FIG. 39 is a view similar to FIG. 38 with the spacer partially inserted between the upper and lower implant bodies with a stabilizing post received between the pair of spaced wings or tabs.
Figure 40:
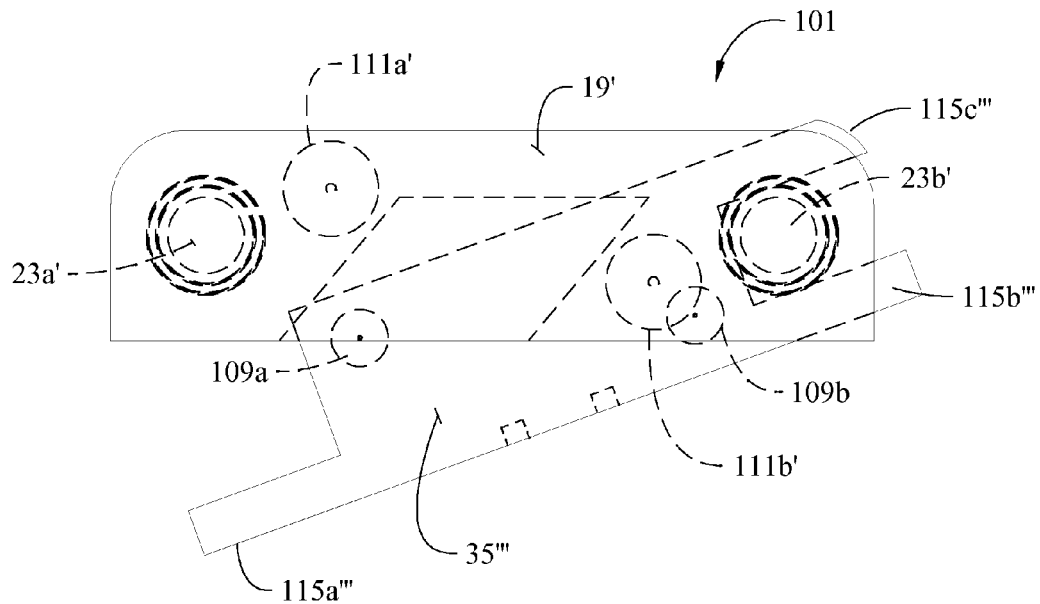
FIG. 40 is a view similar to FIG. 39 showing the spacer partially rotated toward its installed position in which the spacer is substantially parallel to the body members.
Figure 41:
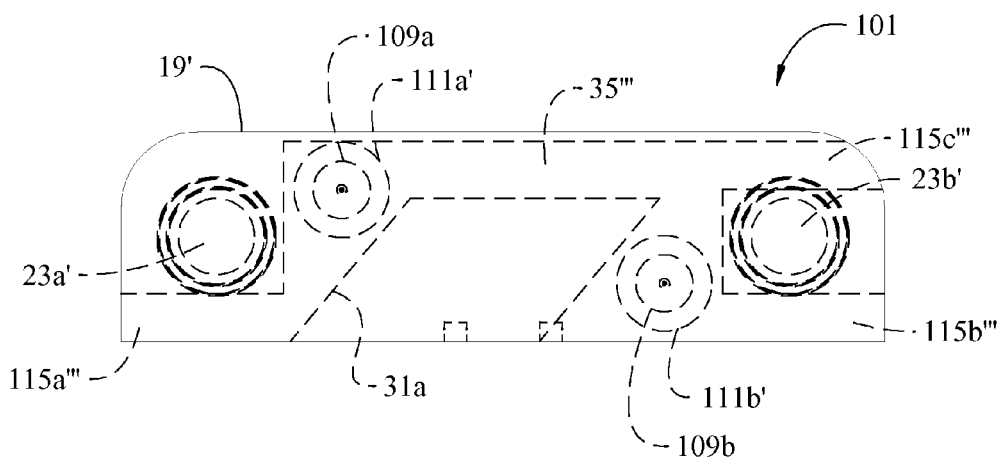
FIG. 41 is a view similar to FIG. 40 showing the spacer in its fully installed position.
Figure 42:
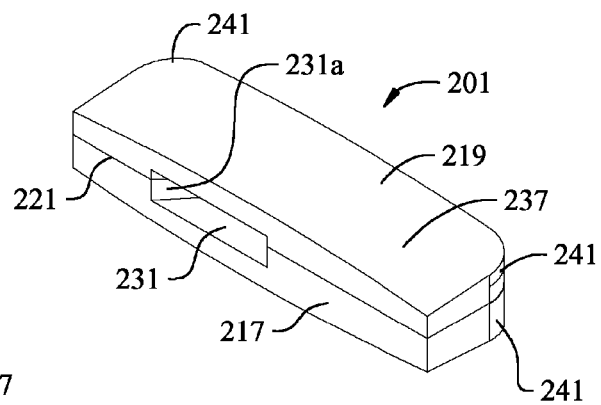
FIG. 42 is a perspective view of another embodiment of an expandable or variable height implant of the present disclosure having angled (tapered) upper and lower surfaces for treating or correcting certain lordotic conditions.
Figure 43:
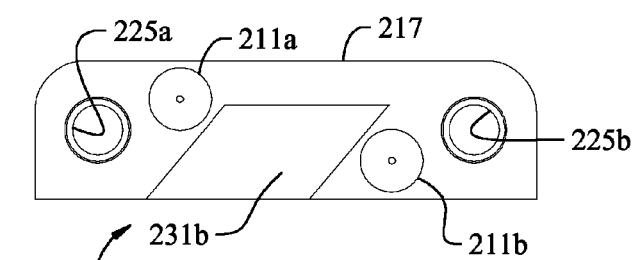
FIG. 43 is a top plan view of the lower body of the implant.
Figure 44:
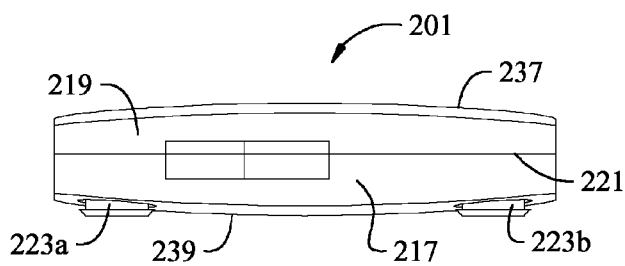
FIG. 44 is a front elevational view of the implant of FIGS. 42 and 43.
Figure 46:
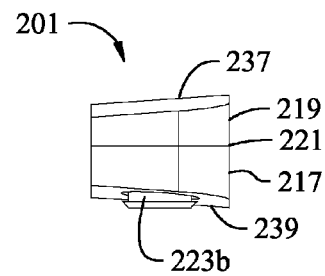
FIG. 46 is a side elevational view of the implant of FIGS. 42-45.
Figure 45:
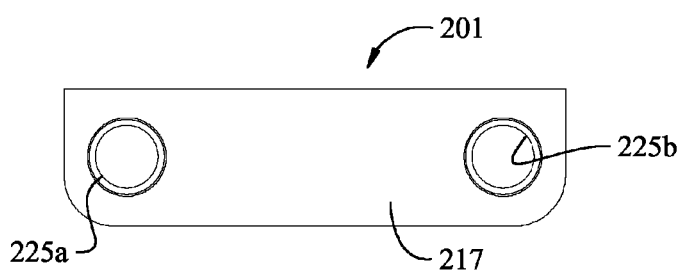
FIG. 45 is a bottom plan view of the implant of FIGS. 42-44.

Referring now to FIGS. 36-41, an alternative embodiment of spacer 35' is shown and is indicated in its entirety at 35'''. This spacer 35''' is shown to have a pair of wings or extensions 115a''', 115b''', one on each lateral end of the spacer, extending laterally from the posterior side of the spacer. In addition, on the right-hand end of the spacer (as shown in FIG. 36) has another wing 115c''' spaced from wing 115b''' with the space therebetween being sufficient so as to readily receive stabilizing post 23b'. The anterior faces of wings or extensions 115a''', 115b''' bear against the posterior faces of posts 23a', 23b' so as to prevent anterior movement of the spacer 35''' beyond its predetermined position, as shown in FIG. 41. In addition the inner or posterior face of wing 115c''' is positioned to engage against post 23b' so as to prevent posterior movement of the spacer 35''. It will be further appreciated that the length of each wing 115a''', 115b''', and 115c''' is such that with the spacer 35''' positioned within space 21' (as shown in FIG. 41) such that one lateral side of the spacer bears against its respective post 23a' or 23b', the wing 115a''' or 115b''' on the opposite lateral side of the spacer still engages the posterior face of its respective post such that both of the wings bear against their respective posts and thus positively prevent insertion of the spacer in anterior direction beyond a desired anterior position relative to the body members 17', 19'.

Figure 38:
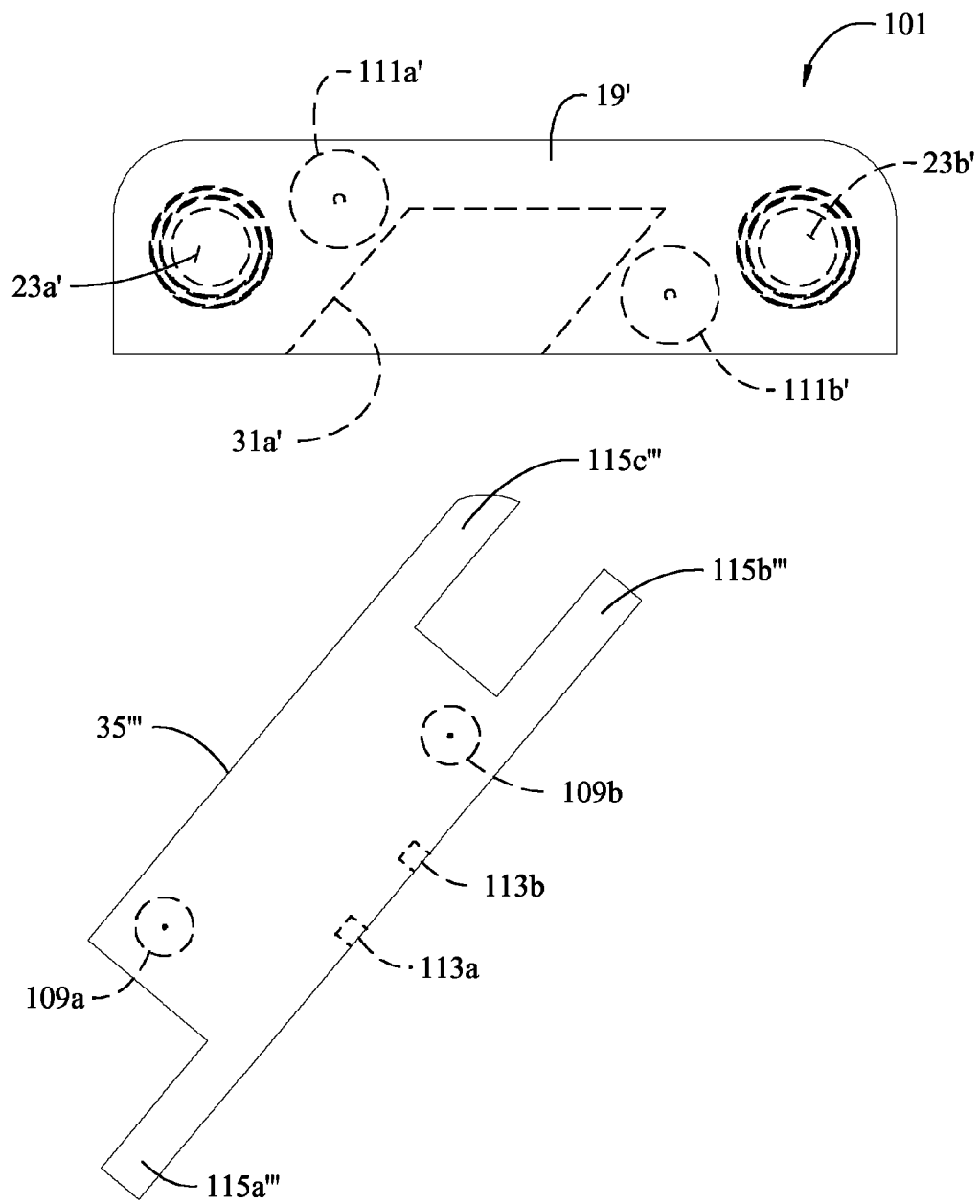
FIG. 38 is a top plan view of the implant and the spacer showing the spacer prior to being inserted between the implant bodies oriented at an angle with respect to the implant body so as to be inserted between the implant bodies.

As shown in FIG. 38, upon installation of spacer 35''', the spacer is oriented at an oblique angle with respect to the implant bodies 17', 19' when the implant bodies are positioned between adjacent vertebrae and with the implant bodies distracted (as generally shown in FIG. 4) so as to receive that spacer inserted through an annulotomy 11 on the opposite side from that shown in FIG. 4. As shown in FIG. 39, the spacer is moved diagonally between body members 17', 19' until post 23b' is received between wings 115b''', 115c'''. Then, as shown in FIG. 40, the spacer is rotated so that the spacer 35''' is rotated clockwise about post 23b' (as shown in FIG. 40) until wing 115a''' bears against the posterior surface of post 23a'. In this position, post 23b' is received between wings 115b''' and 115c''' and wing 115''' bears against the posterior surface of post 23a'.

It will be appreciated that if spacer 35''' is to be inserted through an annulotomy 11 of the opposite side of the disc from that shown in FIG. 4, the spacer 35''' would be oriented to be a mirror image of the spacer 35''' shown in FIG. 38.

With spacer 35''' in the position shown in dotted lines in FIG. 41, the protuberances 109a, 109b are received in recesses 111a, 111b and the body of the spacer is positioned between the posts 23a, 23b'. Then upon retraction of the vertebrae spacing and upon the application of compression loading to the implant 101, the protuberances and the recesses will cooperate, as previously described, so as to self-center and to self-align the spacer relative to the body members. Further, with the protuberances received in their respective recesses and with such normal compression loads applied to the implant, the protuberances and recesses will effectively prevent movement or migration of the spacer relative to the body members. Still further, with bone graft material (not shown) packed within the disc space DS on the posterior side of implant 101, the bone graft material will also aid the protuberances and recesses in preventing movement or migration of the space from between the body members. As noted, the spaced wings 115b''', 115c''' substantially prevent both anterior and posterior movement of the spacer relative to the body members 17', 19' beyond a predetermined limited amount of movement.

It will be further appreciated that implants 1 and 101 may be provided in a range of widths, thicknesses, and lengths to readily accommodate taller disc spaces DS and different vertebrae sizes. For example, implants 1, 101 may have heights ranging between 8.5 mm-10.0 mm, to accommodate taller or shorter disc spaces DS and may have widths ranging between about 11-13 mm., and lengths ranging between about 40-60 mm. to accommodate vertebrae having a larger vertebrae footprint.

Referring now to FIGS. 42-59, three additional embodiments of the implant of the present disclosure are illustrated in which the upper and lower surfaces of the implant are angled (tapered from rear to front) so as to provide options for encountered or desired disc space lordosis. Specifically referring to the embodiment shown in FIGS. 42-47, this is an expandable interbody or implant, as indicated in its entirety by reference character 201. The construction of this interbody or implant 201 is similar to the embodiments discussed above and reference characters 217, 219, etc. indicate parts having a similar construction and operation as similar parts identified by similar reference characters 17, 19 etc. of the embodiment illustrated in FIGS. 1-41. Accordingly, only the primary differences between implant 201 and the above-described embodiments will be described in detail. In FIGS. 42-47, the implant is shown in its collapsed or retracted condition with no spacer 35 installed between the inner surfaces of the lower and upper body members 217 and 219. However, it will be understood that with the implant 201 inserted in disc space DS, as described above, and with the lower and upper body members distracted, a spacer 35, 35', 35'', or 35''' may be inserted within space 221 between the body members in the manner described above.

Figure 47:
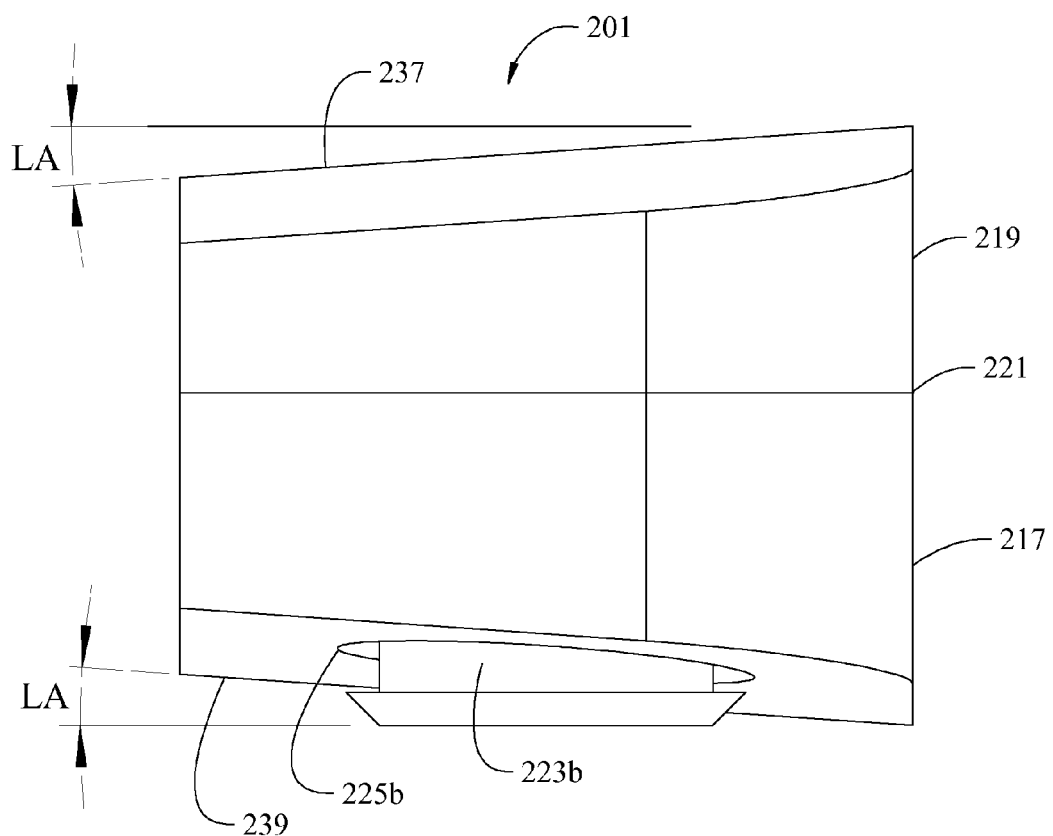
FIG. 47 is a side elevational view of the implant of FIGS. 42-46 on an enlarged scale.
Figure 48:
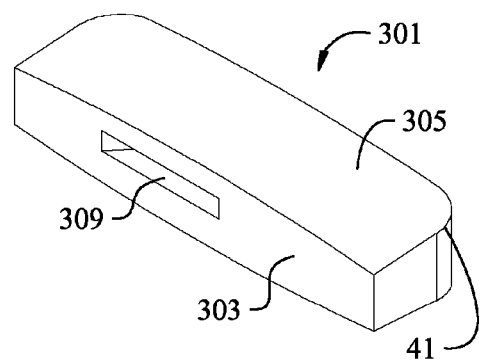
FIG. 48 is a perspective view of still another embodiment of the implant of this disclosure where the implant is not expandable, but rather is of a fixed height, but where such implant has angled or tapered upper and lower surfaces and may be readily utilized in accordance with the methods of this disclosure.
Figure 49:
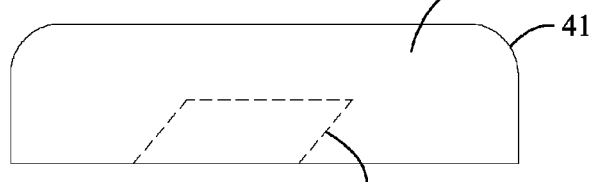
FIG. 49 is a top plan view of the implant of FIG. 48.
Figure 50:
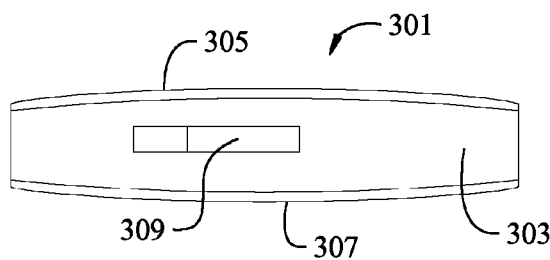
FIG. 50 is a front elevational view of the implant of FIGS. 48, 49.
Figure 52:
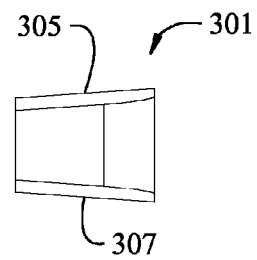
FIG. 52 is a side elevational view of the implant of FIGS. 48-51 illustrated the angles upper and lower surfaces of the implant.
Figure 51:
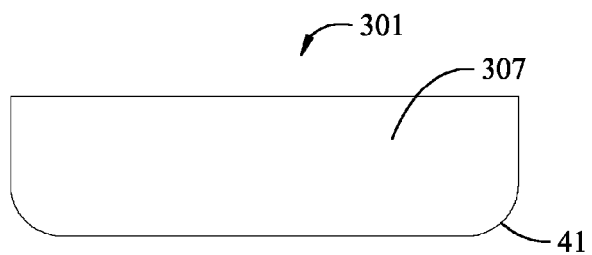
FIG. 51 is a bottom plan view of the implant of FIGS. 48-50.
Figure 53:
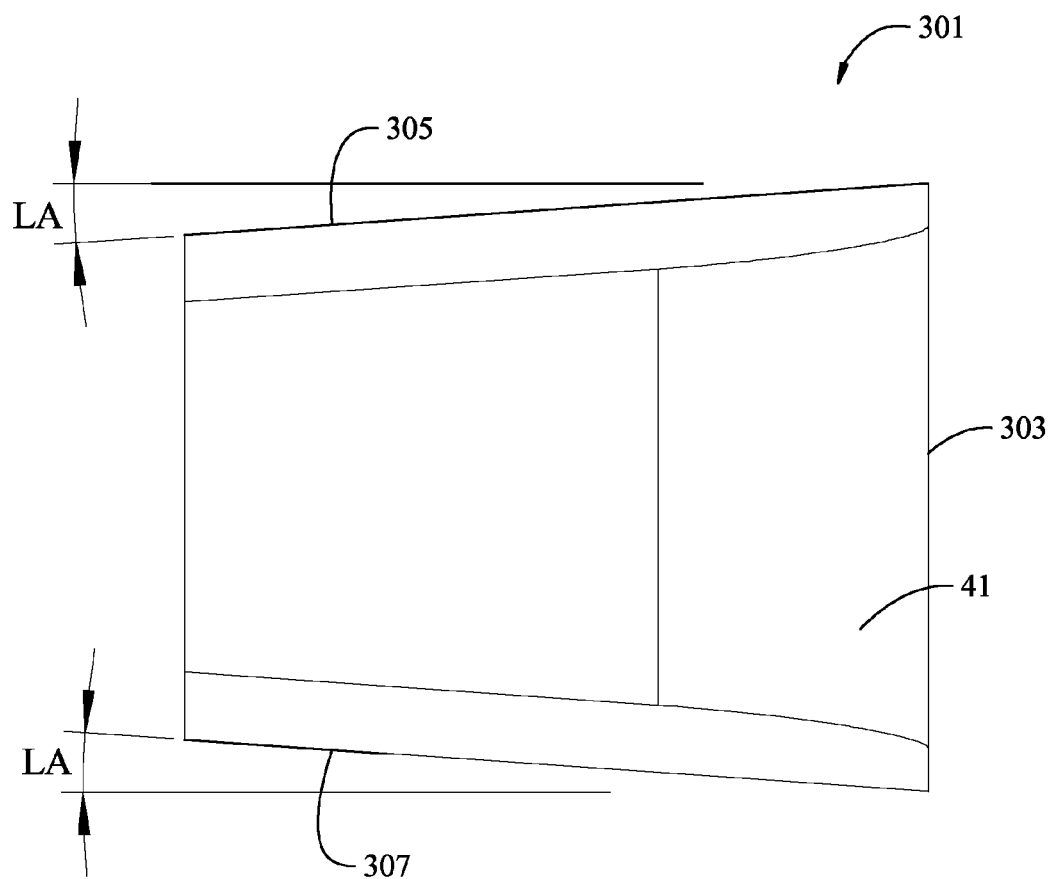
FIG. 53 is a side elevational view of the implant of FIGS. 48-52 on an enlarged scale.
Figure 59:
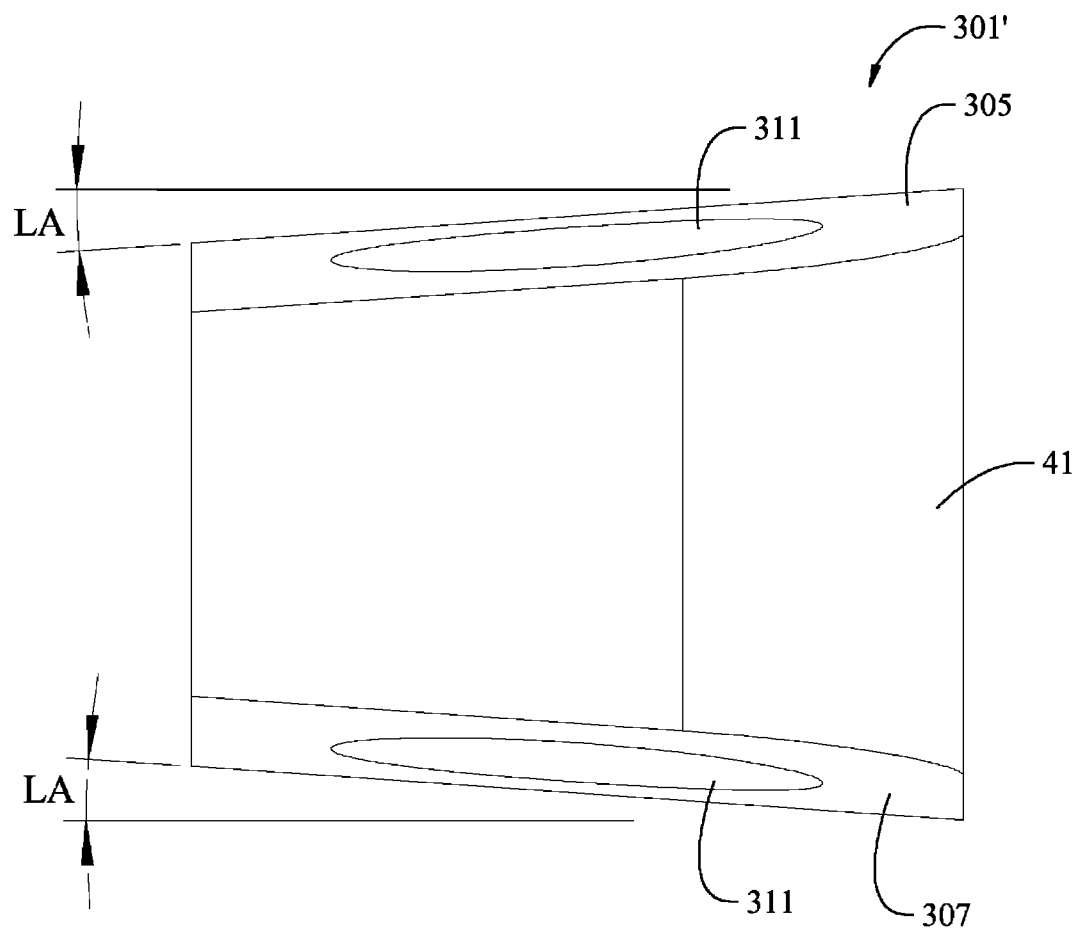
FIG. 59 is a side elevational view of the implant of FIGS. 54-58 on an enlarged scale.

As perhaps best shown in FIG. 47, the upper face 237 of upper body member 219 and the lower face 239 of lower body member 217 are angled or tapered from rear to front at a lordotic angle LA. The lordotic angles of various implants 201 may range between about 0° and about 12°. It will be appreciated that the lordotic angles of the upper and lower body members may be different. Thus, upon encountering a patient having disc space lordosis, implants 201 having the desired lordotic angles LA, as chosen by the surgeon, may be used so as to reconstruct the spine by maintaining segmental lordosis, regional lordosis, and global sagittal balance. More specifically, upon encountering a need to improve the segmental or disc space lordosis, an implant 201 having a desired predetermined lordosis angle LA may be installed in disc space DS so that with the implant distracted, with an appropriate spacer 35, 35', 35'', or 35''' installed in space 21 between the lower and upper body members, with upper and lower faces 237, 239 of the implant engaging the cortical rims CR of the adjacent vertebrae bodies, and with the angled, convex shape of the upper and lower faces of the implant generally conforming to the disc space and contacting the vertebrae endplates, upon distracting the adjacent vertebrae bodies, the desired amount of lordotic correction may be introduced in the reconstructed disc spacer. It will be also appreciated that because the implant 201 is supported by the cortical rims CR of the vertebrae bodies, there is less of a tendency for subsidence to occur with a consequent loss of disc space height to preoperative levels.

Referring now to FIGS. 49-53, still another embodiment of a non-expandable or fixed height interbody implant in accordance with the present disclosure is shown. This implant is indicated in its entirety by reference character 301. As noted, implant 301 is non-expandable or of fixed height and thus has a one-piece body 303 having an upper surface 305 and a lower surface 307. The rear face of body 303 has a slot 309 therein similar to slot 31 of the above embodiments so that the implant maybe inserted into the disc space DS through annulotomy 11 and maneuvered within the disc space by the surgeon so that the ends of the implant bear on the cortical rims CR of the adjacent vertebrae bodies and such that the implant is positioned generally similar to implant 1, as illustrated in FIG. 4. The upper and lower faces 305 and 305 are angled or tapered in a manner similar to implant 201 such that these upper and lower faces have a lordotic angle LA, which may range from about 0° to about 12°. Of course, the lordotic angles LA of implant 301 may be used to maintain or correct disc space lordosis in the same manner as described in regard to implant 201.

Turning now to FIGS. 54-59, still another embodiment of the present disclosure is illustrated in its entirety at 301'. This implant 301' is similar to implant 301, as above described, except that it has openings or fenestrations 311 formed therein for the purpose of bone growth or fusion through the implant. This augments the bone graft the surgeon places posterior to the implant for fusing or permanently joining the vertebrae bodies above and below the disc space.

As various changes could be made in the above constructions and methods without departing from the scope of the disclosure, it is intended that all matter contained in the above description or shown in the accompanying drawings shall be interpreted as illustrative and not in a limiting sense.

The invention claimed is:

1. A method of installing and using an implant to distract and stabilize a disc space between two adjacent vertebrae so as to enable bone graft material to fuse said adjacent vertebrae, said vertebrae each having a cortical rim and an endplate, said adjacent vertebrae having an annulus and a disc space therebetween, said implant having an elongate body of a length sufficient to extend laterally across said cortical rims of the adjacent vertebrae bodies and to be at least in part engaged by said cortical rims of said adjacent vertebrae bodies, said implant body having an upper surface and a lower surface, said method comprising the steps of:
   a. making a posterolateral incision in said annulus at the desired level to access disc space between the adjacent vertebrae to be fused;
   b. performing a discectomy of the disc material within the annulus via said incision in said annulus;
   c. preparing the endplates of said adjacent vertebrae bodies;
   d. forming a first opening in the anterolateral side of said annulus generally opposite said incision;
   e. forming a second opening in the anterolateral side of said annulus generally opposite said first opening;
   f. selecting said implant such that the upper and lower surfaces of said implant have a desired lordotic angle;
   g. inserting said implant into said disc space via said incision;
   h. installing a first end of said implant in said first opening;
   i. installing a second end of said implant in said second opposite opening such that said implant extends generally laterally of said vertebrae bodies and is at least in part engaged by the cortical rims of said vertebrae bodies;
   j. distracting said disc space a desired amount; and
   k. retracting said adjacent vertebrae bodies such that said upper and lower faces of said implant are supported on the cortical rims of said adjacent vertebrae bodies such that said lordotic angles introduce a desired amount of segmental lordosis in the reconstructed disc space.

2. The method of claim 1 wherein said incision is an oblique annulotomy made in the posterior lateral portion of said annulus.

3. The method of claim 1 wherein said implant is a fixed height implant.

4. The method of claim 1 wherein said implant having one or more fenestrations for promoting bone growth through the implant.

5. The method of claim 1 wherein the upper and lower surfaces of said implant may have a lordotic angle ranging between about 0 degrees and 12 degrees.

6. A method of installing and using an implant to distract and stabilize a disc space between two adjacent vertebrae so as to enable bone graft material to fuse said adjacent vertebrae, said vertebrae each having a cortical rim and an endplate, said adjacent vertebrae having an annulus and a disc space therebetween, said implant having an elongate body of a length sufficient to extend across said cortical rims of the adjacent vertebrae bodies and to be at least in part engaged by said cortical rims of said adjacent vertebrae bodies, said implant body having a lower body member and an upper body member movable toward and away from one another such that when said body members are moved away from one another a space is formed therebetween, said method comprising the steps of;
   a. making a posterolateral incision in said annulus at the desired level to access disc space between the adjacent vertebrae to be fused;
   b. performing a discectomy of the disc material within the annulus via said incision in said annulus;
   c. preparing the endplates of said adjacent vertebrae bodies;
   d. forming a first opening in the anterolateral side of said annulus generally opposite said incision;
   e. forming a second opening in the anterolateral side of said annulus generally opposite said first opening;
   f. selecting said implant such that the upper and lower surfaces of said implant have a desired lordotic angle;
   g. inserting said implant into said disc space via said incision;
   h. installing a first end of said implant in said first opening;
   i. installing a second end of said implant in said second opening such that said implant extends generally across said vertebrae bodies and such that said implant is at least in part engaged by the cortical rims of said vertebrae bodies proximate said first and second openings;
   j. after said implant is installed in said disc space, distracting said implant bodies a desired amount;
   k. inserting a spacer within said space between said upper and lower body members;
   l. retracting said adjacent vertebrae bodies such that said upper and lower body members of said implant are at least in part engaged by the cortical rims of said adjacent vertebrae bodies, such that said spacer maintains a desired amount of distraction of said adjacent vertebrae bodies, and such that said lordotic angles introduce a desired amount of segmental lordosis in the reconstructed disc space; and
   m. placing bone graft material within said disc space so as to fuse said adjacent vertebrae.

* * * * *